United States Patent
Moghadam

(10) Patent No.: US 12,337,477 B2
(45) Date of Patent: Jun. 24, 2025

(54) ROBOTIC ULTRASOUND

(71) Applicant: KENNESAW STATE UNIVERSITY RESEARCH AND SERVICE FOUNDATION, INC., Kennesaw, GA (US)

(72) Inventor: Amir Ali Amiri Moghadam, Marietta, GA (US)

(73) Assignee: Kennesaw State University Research And Service Foundation, Inc., Kennesaw, GA (US)

( * ) Notice: Subject to any disclaimer, the term of this patent is extended or adjusted under 35 U.S.C. 154(b) by 0 days.

(21) Appl. No.: 18/459,205

(22) Filed: Aug. 31, 2023

(65) Prior Publication Data

US 2024/0066689 A1    Feb. 29, 2024

Related U.S. Application Data

(60) Provisional application No. 63/402,554, filed on Aug. 31, 2022.

(51) Int. Cl.
*B25J 9/16* (2006.01)
*B25J 9/00* (2006.01)
*B25J 9/10* (2006.01)

(52) U.S. Cl.
CPC .......... *B25J 9/1623* (2013.01); *B25J 9/0015* (2013.01); *B25J 9/1075* (2013.01); *B25J 9/1664* (2013.01)

(58) Field of Classification Search
CPC ........ B25J 9/003; B25J 9/0015; B25J 9/1075; B25J 9/1623
See application file for complete search history.

(56) References Cited

U.S. PATENT DOCUMENTS 7,172,385 B2 * 2/2007 Khajepour ............ B25J 9/0078
                                                        901/29
2023/0339106 A1 * 10/2023 Lu ..................... B25J 9/1625

FOREIGN PATENT DOCUMENTS

| CN | 110815178 A | * | 2/2020 | ............... B25J 9/00 |
| CN | 114393567 A | * | 4/2022 | |
| CN | 114211475 B | * | 10/2023 | ............. B25J 9/003 |

* cited by examiner

*Primary Examiner* — Bobby Rushing, Jr.
(74) *Attorney, Agent, or Firm* — Smith, Gambrell & Russell LLP

(57) ABSTRACT

An apparatus is described for robotic control of an ultrasound imaging device. The apparatus comprises a fixed base and a movable platform with an end-effector. A plurality of passive soft links connects the platform to the base. A series of cables connect the platform to a set of motors adjacent the base. When the platform is at rest, the tension in the cables counter-balances the passive soft links pushing the platform away from the base plate. Control electronics move the motors so as to control the location and the orientation of the platform. By increasing or decreasing tension in the cables, the motors smoothly control the location and the orientation of the platform and thus the end effector. Such a robotic apparatus can be used to provide expert handling of an ultrasound imaging device remotely.

6 Claims, 19 Drawing Sheets

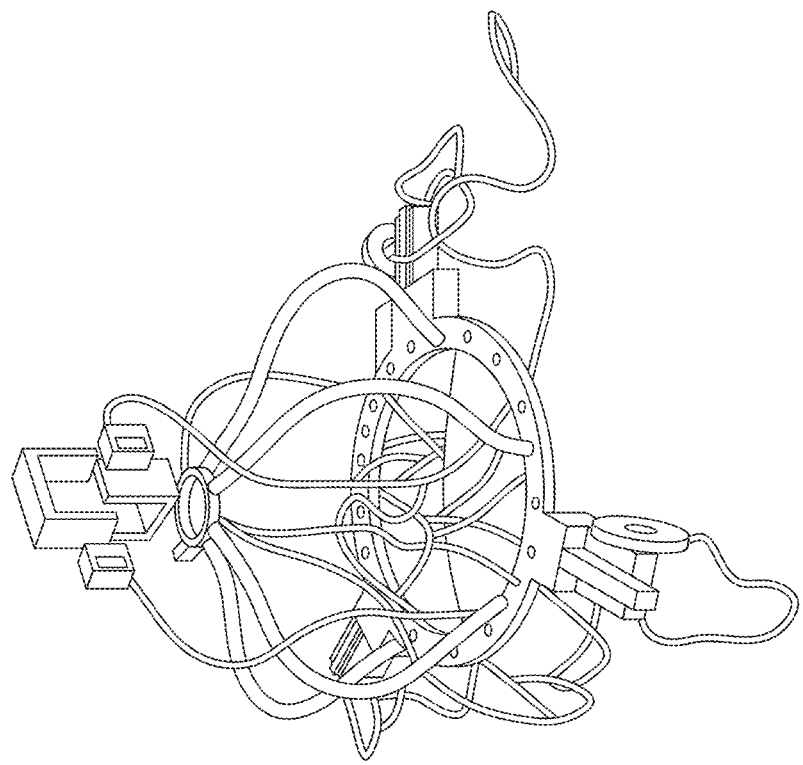
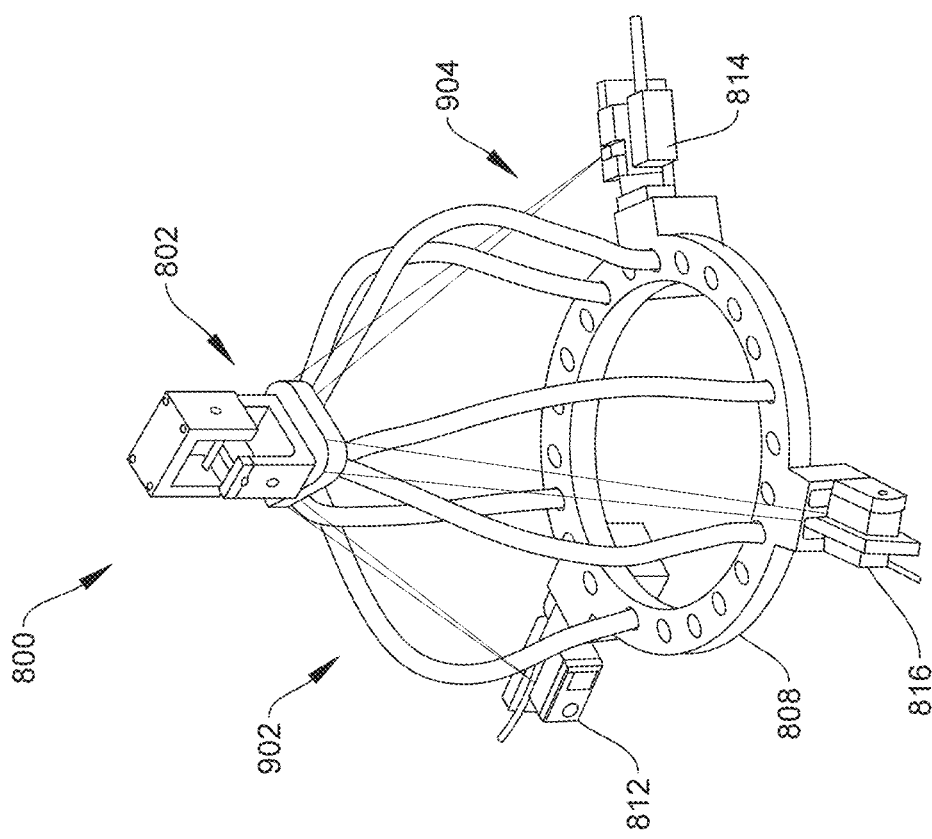
FIG. 13

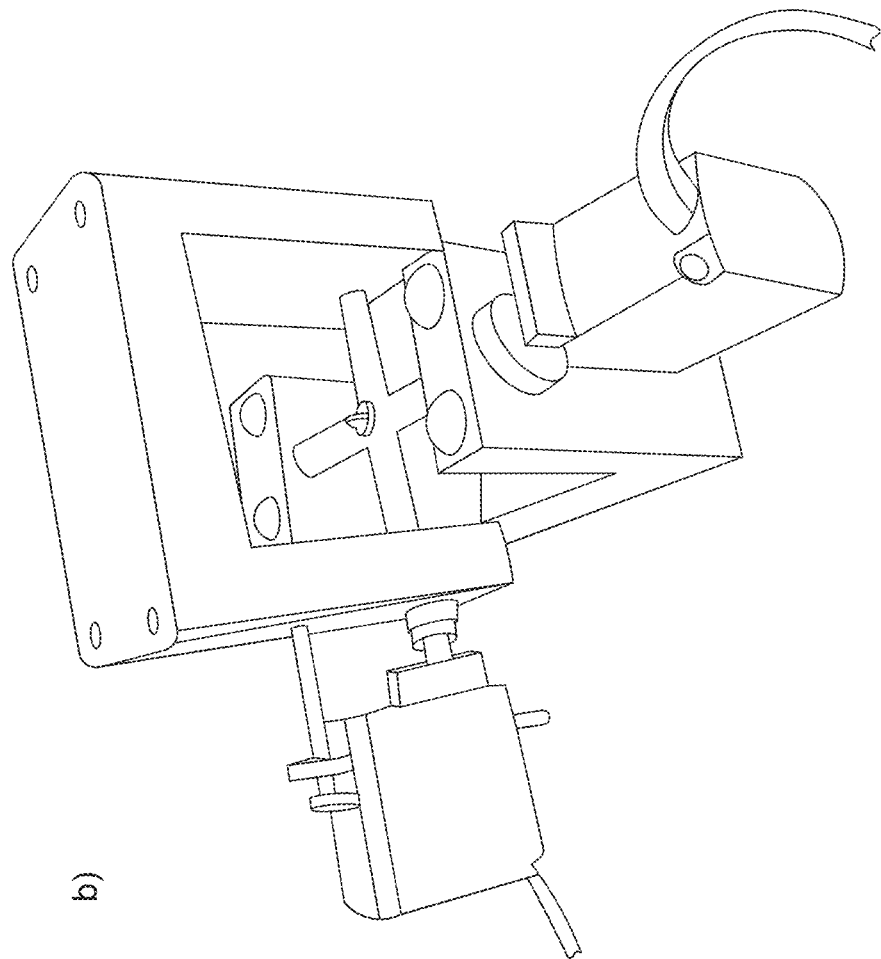
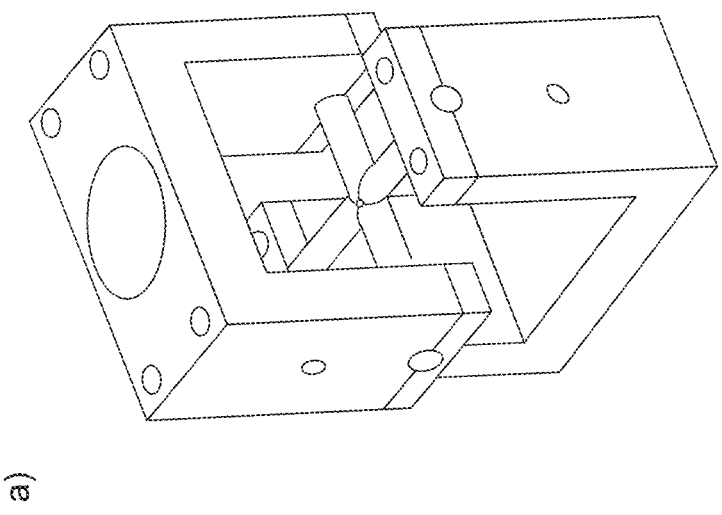
FIG. 14

ROBOTIC ULTRASOUND

CROSS-REFERENCE TO RELATED PATENT APPLICATION

The present patent application claims priority to U.S. Provisional Application No. 63/402,554, filed on Aug. 31, 2022, and entitled "Robotic Ultrasound", the disclosure of which is incorporated herein by reference thereto in its entirety.

This invention was made with government support under R15EB032189 awarded by the National Institutes of Health. The government has certain rights in the invention.

BACKGROUND

Ultrasound imaging procedures are one of the least invasive and most cost-effective imagining modalities widely being used in diagnostic applications. It would be beneficial to have a soft robot be able to apply enough force for a technician to perform an ultrasound remotely without any potential for damage to a patient.

Soft robotics has the potential to greatly improve the interaction of human and robotic systems due to the application of soft and compliant materials in the structure of the robot. Since force sensors cannot ensure the safety of humans in a human-robot interaction, the application of soft and lightweight materials in the structure of the robot may be used to minimize the impact forces due to an accidental collision between the robot and the patient. As mentioned, soft robots exist for ultrasound imaging. However, existing soft robots for ultrasound imaging have limited degrees of freedom (DOF) and cannot control both the position and the orientation of the ultrasound probe. Clinical data shows that effective ultrasound imaging of the heart and the abdomen requires 6 DOF. Also, considering the structure of the robot as a single soft arm, the output force and positioning accuracy is limited. While the application of a parallel structure may improve the blocking force and the positioning accuracy of the system, such a system only has 3 DOF and suffers from the problem of limited maneuverability.

Accordingly, there is a need for a steerable ultrasound probe with a high level of maneuverability, precise positioning, and sufficient blocking force while still being soft and compliant so as to avoid any possibility of injury to a patient while in use.

SUMMARY

A 6 DOF soft robot is disclosed. The soft robot may comprise a plurality of soft actuators. The soft robot may be utilized for ultrasound imaging, potentially improving patient safety.

A device may comprise a controllable platform, one or more arms, a base, and a controller. The one or more one or more arms may be coupled to the platform and configured to facilitate controlled movement of the platform in multiple degrees of freedom, wherein the one or more arms comprise at least one flexible link. The base may be spaced from the platform and coupled to the one or more arms. The controller may be operationally coupled to the at least one flexible link and configured to cause movement of the at least one flexible link to control one or more of an orientation or a position of the platform.

The flexible links may be made from materials comprising thermoplastic polyurethane, or the like. The flexible links may be soft tendon driven actuators. The flexible links may be soft pneumatic actuators. The device may further comprise a joystick controller for controlling the motion in 6 DOF. The joystick controller may use quantitative feedback theory. The joystick controller may be a Stewart mechanism. One or more linear potentiometers may be mounted onto the one or more onto the legs of the Stewart mechanism. The device may be further configured to cover an area above an abdomen of a patient. The device may further comprise an ultrasound imaging apparatus. Also disclosed is a method of making the device described above.

An apparatus may comprise: a base, a platform comprising an end-effector, one or more arms, one or more motors adjacent to the base, one or more cables, and a controller for actuating the one or more motors. The one or more arms may connect the platform to the base, and the one or more arms may comprise a flexible link and a passive link. The one or more cables may connect the one or more flexible links to the one or more motors. The controller may actuate the one or more motors to controllably decrease or controllably increase the tension in the one or more cables and thereby flex each flexible link as needed to move the end-effector to a selected location and to rotate the end-effector to a selected orientation.

The one or more arms may be arranged in a threefold symmetric pattern around the base. The one or more arms may be fabricated using a 3D printed thermoplastic. The end-effector may comprise an ultrasound imaging apparatus. Tension for a selected one or more cables may be controlled by a selected one or more motors. The apparatus may further comprise a feedback means for controlling the location and the orientation of the end-effector. The feedback means may comprise an electromagnetic tracker. In addition, a method of making the apparatus as described above is also disclosed.

A soft, cable-driven parallel robot apparatus is disclosed comprising: a base, a movable platform comprising an end-effector, one or more passive soft links, one or more motors adjacent to the base, one or more cables, and a controller for actuating the one or more motors. The one or more passive soft links may connect the platform to the base, and the one or more passive soft links may be in compression to push the platform away from the base. The one or more cables may be connected to the platform and also connected to the one or more motors. The controller may actuate the one or more motors to controllably decrease or controllably increase a tension in the one or more cables, whereby the one or more passive soft links move the end-effector to a selected location.

The one or more passive links may be arranged in a threefold symmetric pattern around the base. The apparatus may further comprise one or more motor-controlled universal joints for orienting the end-effector. The end-effector may comprise an ultrasound imaging apparatus. The controller may actuate the one or more motors to provide tension for the one or more cables to place the end-effector in a selected location. The controller may further actuate the one or more motors to provide tension for the one or more cables to place the end-effector in a selected orientation. The apparatus may further comprise a feedback means for controlling the selected location and the selected orientation of the end-effector. The feedback means may comprise an electromagnetic tracker. In addition, a method of making the soft, cable-driven robot apparatus is also disclosed.

BRIEF DESCRIPTION OF THE DRAWINGS

The attached Appendices are hereby incorporated in their entirety. The following drawings show generally, by way of example, but not by way of limitation, various examples discussed in the present disclosure. In the drawings:

FIG. 13 illustrates a six-link design and a fabricated 6-link soft cable-driven robot.

FIG. 14 illustrates two intersecting joints to make a 2D universal joint.

DETAILED DESCRIPTION

Figure 1:
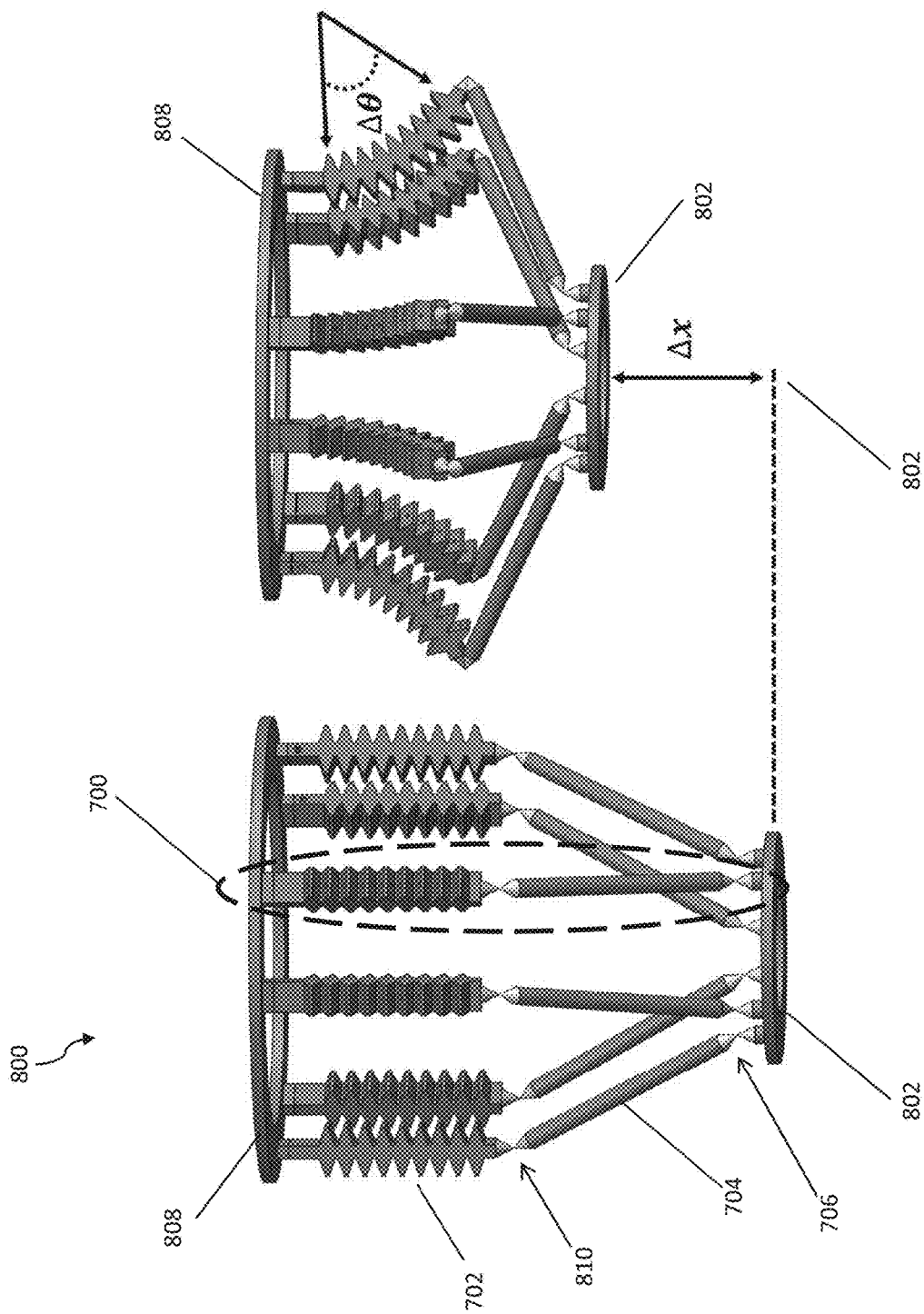
FIG. 1 shows an exemplary mechanical design of a soft robot structure.

Soft robotics is an emerging field of research. Typically, soft robots are made of serial elastomeric arms. However, the application of a parallel structure in the design of a soft robot would be of great interest since it can provide more control on the overall stiffness and the payload of the robot. A 6 degrees-of-freedom (6 DOF) soft robot for use in ultrasound applications is disclosed.

Ultrasound imaging procedure is one of the least invasive and most cost-effective imagining modalities which is widely being used in diagnostic applications. Ultrasound imaging is defined as application of high-frequency sound waves to view inside the body. This technique can be used for real-time imaging and unlike X-ray imaging there is no exposure to harmful ionizing radiation. The Food and Drug Administration lists common ultrasound procedures as abdominal ultrasound, bone sonometry, breast ultrasound, echocardiogram, fetal ultrasound, and ultrasound-guided biopsies. To obtain ultrasound images, clinicians manually steer the ultrasound probe over the region of interest. Thus, the quality of ultrasound images is highly determined by human factors. A study on the accuracy of ultrasound imaging indicates that extended training for postgraduates can improve the accuracy of the images from 65% to about 95%. Also, direct contact between the physicians and patients during the procedure increases the risk of infectious diseases. In the case of a pandemic this can be catastrophic. For instance, the WHO estimated that 115,000 healthcare workers have died from COVID-19. This could have been potentially avoided by acquiring robotic assisted remote diagnostic and therapeutic methods as described herein. There are many other reasons why a robotic assisted remote ultrasound system as described herein might be beneficial such as: people who are living in rural areas may not have access to a skillful sonographer, reduction of the human errors and waiting time, and economical reasons.

Robotic assisted ultrasound imaging has been used in certain applications. These systems generally consist of a robotic arm equipped with an ultrasound probe and a joystick to control the motion of the robot arm. Thus, a physician can remotely steer the ultrasound probe over the region of interest without being in contact with the patient for diagnostic purposes. These robotics systems can be categorized into conventional rigid robots and soft robots. The rigid robots comprise rigid metallic parts and heavily rely on application of external force sensors and monitoring systems to improve the safety of the system. However, if these systems fail when a rigid robot arm is in direct contact with the patient, the result can be catastrophic. Tele-operated robot-assisted ultrasound (US) scanning has been studied sin8ce the late 1990s. Robotic assistance enhances precise position control of the US probe, making the US imaging procedure repeatable and less user-dependent. The execution of operator-robot cooperative control (also known as co-robotic) systems has also been considered, and various robotic systems have been introduced for US application. Typically, rigid serial manipulators used in industry settings, such as the UR robots and KUKA robotics, have been primarily used to move the US probe.

While the safety of such robots is maintained through the software and force sensors, the inherent capability of providing a high blocking force increases the collision risk for the clinical application. Some robotic remote US systems, (e.g., MELODY, AdEchoTech, Naveil, France), divide the scanning workspace into two phases: (i) initial US placement and (ii) finer tuning. The operation safety risk may be reduced by limiting the blocking force at the second phase.

One example of a soft robot is a soft arm with 3 degrees of freedom (DOF). Noting that the minimum required DOF for manipulation in 3-dimensional spaces is 6, this system suffers from limited maneuverability and cannot effectively perform imaging procedures.
Overcoming the Limitations of Existing Soft Robots for Ultrasound Imaging.

The minimum required DOF for manipulation in 3D spaces is six (e.g., three translational motions (x, y, and z) and three rotational motions (roll, pitch, yaw)). Existing soft robots for ultrasound imaging only provide 3 DOF, which is not sufficient for effective manipulation in complex 3D ultrasound procedures. Thus, a six DOF soft parallel robot is disclosed, which can be used for remote ultrasound imaging, for instance prenatal fetal ultrasound imaging. The disclosed robotic system has six DOF and can control both the position and orientation of the ultrasound probe which improves its dexterity.
Description of Structure and Component of the Soft Parallel Robot.

Disclosed herein is a six DOF soft parallel robot which is inspired by the structure of a rigid Stewart robot. A Stewart mechanism is well known for its use in flight simulators. A Stewart mechanism may have 6 degrees of freedom and can move the upper platform in both the x, y, and z directions and the three angular orientations, roll, pitch, and yaw. A Stewart mechanism comprises a rigid upper platform, six joints linking the rigid upper platform with six legs, and six linear actuators, one attached to each leg. In this example, the legs may telescope into themselves, allowing the linear actuators to extend or retract each leg independently of the others. To transform the rigid structure of the Stewart mechanism to its analogous soft parallel robot, linear actuators (electromotors) and rigid links are first replaced with active soft links (tendon driven actuators with one DOF). Next, the rigid universal joints are replaced with flexible links and possibly also with a passive link. The proposed changes in the components of the Stewart mechanism make the robot structure soft and compliant so that it can safely interact with patients during the ultrasound scanning procedure.

In an alternative configuration, a Stewart mechanism may act as a controller for the soft robot, much as a joystick. In such a configuration, the linear actuators would be swapped out with linear potentiometers to measure the displacement of each leg. Each leg may be connected to the bottom rigid platform through a universal joint which can rotate around two axes. The Stewart mechanism may include universal joints especially the two axes of rotation available to each leg where it may be joined to the bottom platform. The linear actuators may be replaced by linear potentiometers to measure displacement of the legs. In concept, a Stewart mechanism may be similar to the 3-universal-spherical-revolute (3USR) robot.

A nonlinear complex kinematics model of the soft robot is provided to demonstrate how the soft robot may move in arbitrary three-dimensional trajectories. The design of a soft robot provides a high level of maneuverability for 3D ultrasound interventions. The soft robot comprises two main body parts which are connected through soft links and compliant joints or mechanisms. Any mechanism that has the tendency to bend is considered a compliant mechanism; in other words, the input force, torque, or displacement is transferred from one point to another point on the mechanism through the deformation of its flexible members rather than the revolute motion between the rigid links. Fully compliant mechanisms do not involve any joints and may be designed as a single piece. These types of mechanisms are generally limited to small ranges of displacement. Semi-compliant mechanisms include both compliant parts and traditional rigid links and joints. Compliant mechanisms can accomplish motions that may be difficult and expensive to achieve by rigid-body mechanisms by exploiting the flexibility of their components. The advantages of compliant mechanisms over traditionally designed rigid mechanisms include simplified design and improved performance. Simplified design implies a reduced number of links, lowers cost, and simplifies manufacturing processes, whereas improved performance can be achieved by lowered friction, larger deformations, reduced wear, and reduced lubrication requirements (or none at all). Compliant mechanisms have been receiving increasing attention due to their inherent properties and monolithic manufacturability in micro and nanoscale. Additionally, light-weight systems are desired in aerospace applications, and so distributed or lumped compliant designs serve as good candidates exhibiting high performance.

A method for designing a soft robot as disclosed herein may include: (1) data acquisition and processing, (2) developing a theoretical model, (3) 3D printing an initial prototype of the soft robot, (4) iterating the design and fabricating the final product, and (5) evaluating and validating performance.

Aim 1: Design and Fabrication of a 6 DOF Soft Robot for Safe Ultrasound Imaging.

Design objectives. The robot must have 6 DOF, the workspace must cover an area of interest above the abdomen of the patient, and an overall stiffness of soft robot must be designed in a way that it can only apply forces within an acceptable range for a patient. To obtain the required range of movement and force levels for the robot, manual scanning on an abdominal ultrasound phantom may be performed using a handheld ultrasound probe equipped with position and force sensor. A standard ultrasound probe (X6-1, Philips, Amsterdam, Netherlands) and scanner (EPIQ7, Philips, Amsterdam, Netherlands) may be used. To integrate the sensors with the probe, a 3D printed holder may be designed. The position sensor may be an electromagnetic (EM) tracking sensor (Aurora, NDI, Ontario, Canada) and the force sensor is a six-axis force-torque sensor (Nano 17, ATI, Apex, USA).

Design process. A first step in designing a 3D printed prototype of the soft robot is to derive the kinematics equations, followed by using these equations to optimize the size of robot components so that the robot satisfies the design objectives in terms of workspace and required DOF. Next, knowing the required range of forces from sensory data the mechanical stiffness of the soft robot should be designed in a way that it can apply the required forces for successful imaging and does not cause discomfort during the procedure. A robot can be considered as a nonlinear spring (FIGS. 1-2) where its stiffness depends on the shape and material property of the soft links. To explain this process, an analogous linear spring system is used. Once, the displacement range of the spring is determined from workspace constraints, the stiffness of the spring may be optimized so that for the given range of its displacement it can satisfy the constraints on the required blocking force of the system (FIG. 2). The optimization process may be performed using finite element methods (FEM) and may be validated using a 3D printed model and force sensors. The dynamics of the robot may be derived and simulated using MATLAB. Considering the highly nonlinear dynamics of the soft robot, a robust controller using Quantitative Feedback Theory (QFT) may be designed for robust position control of the robot. QFT is one of the most powerful robust control techniques which can consider both parameter and structure uncertainties. The final design of the robot may be 3D printed with polymeric materials such as thermoplastic polyurethane (TPU).

Figure 2:
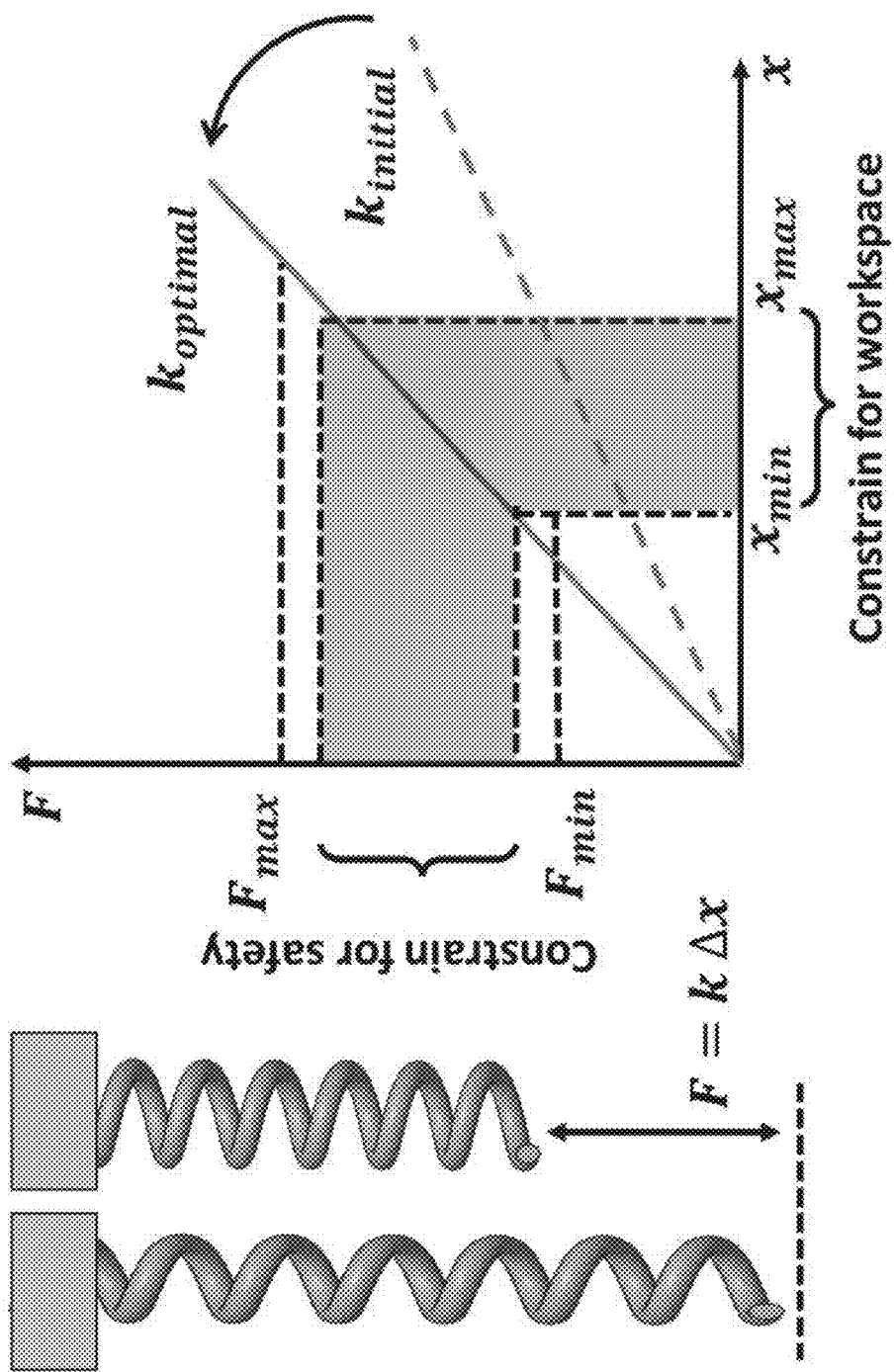
FIG. 2 shows a spring model of a soft robot structure.

FIG. 1 shows the soft robot as a nonlinear spring which is required to have proper longitudinal and shear stiffness. FIG. 2 illustrates an analogous linear spring example to explain the design process: once the required range of motion is obtained from the kinematic model, the stiffness of the spring can be optimized to satisfy the constraint on the required blocking force of the system.

Aim 2: Development of an Intuitive Mechanism for Position Control of the Robot.

Design objectives: The joystick must have 6 DOF, be fully controlled with one hand, and be intuitive to use. Also, for convenience the workspace of the joystick should take up a small volume within the range of sonographer's hand motion.

Figure 3:
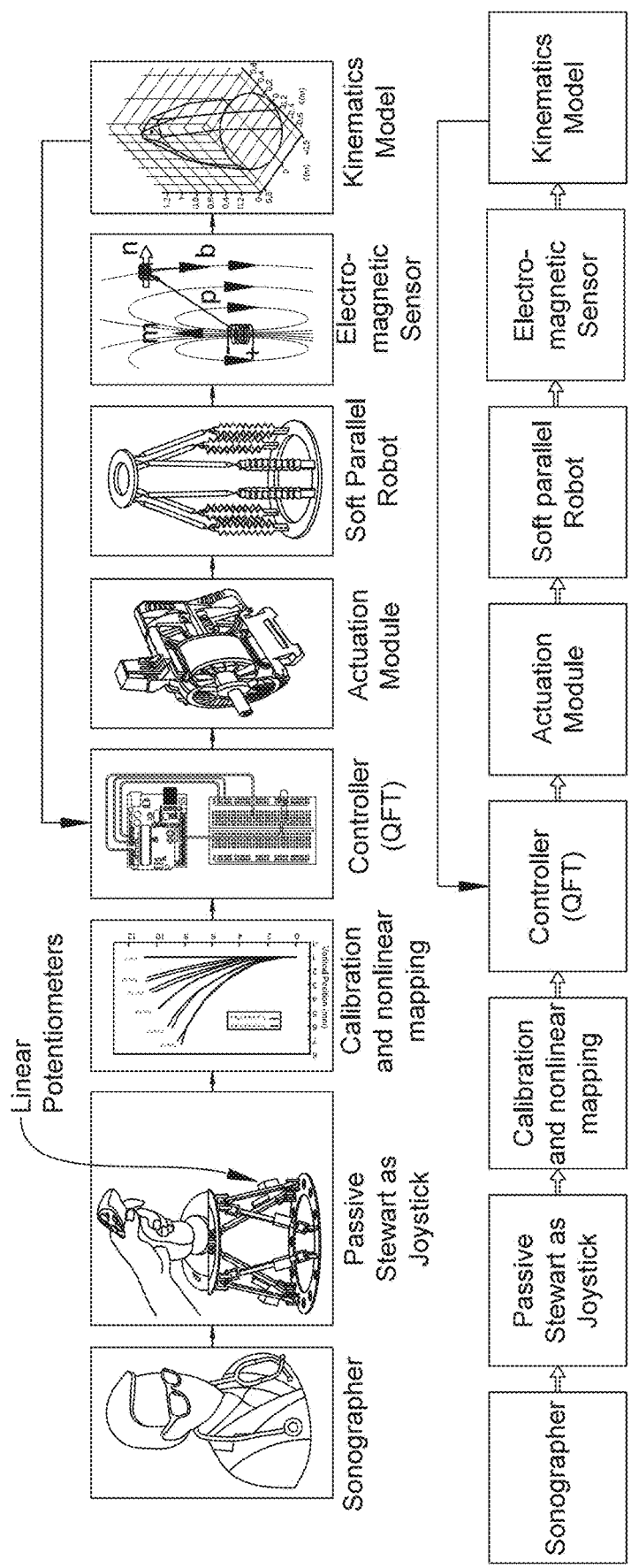
FIG. 3 shows components of an intuitive user interface for position control of the soft robot using a passive Stewart mechanism.
Figure 4:
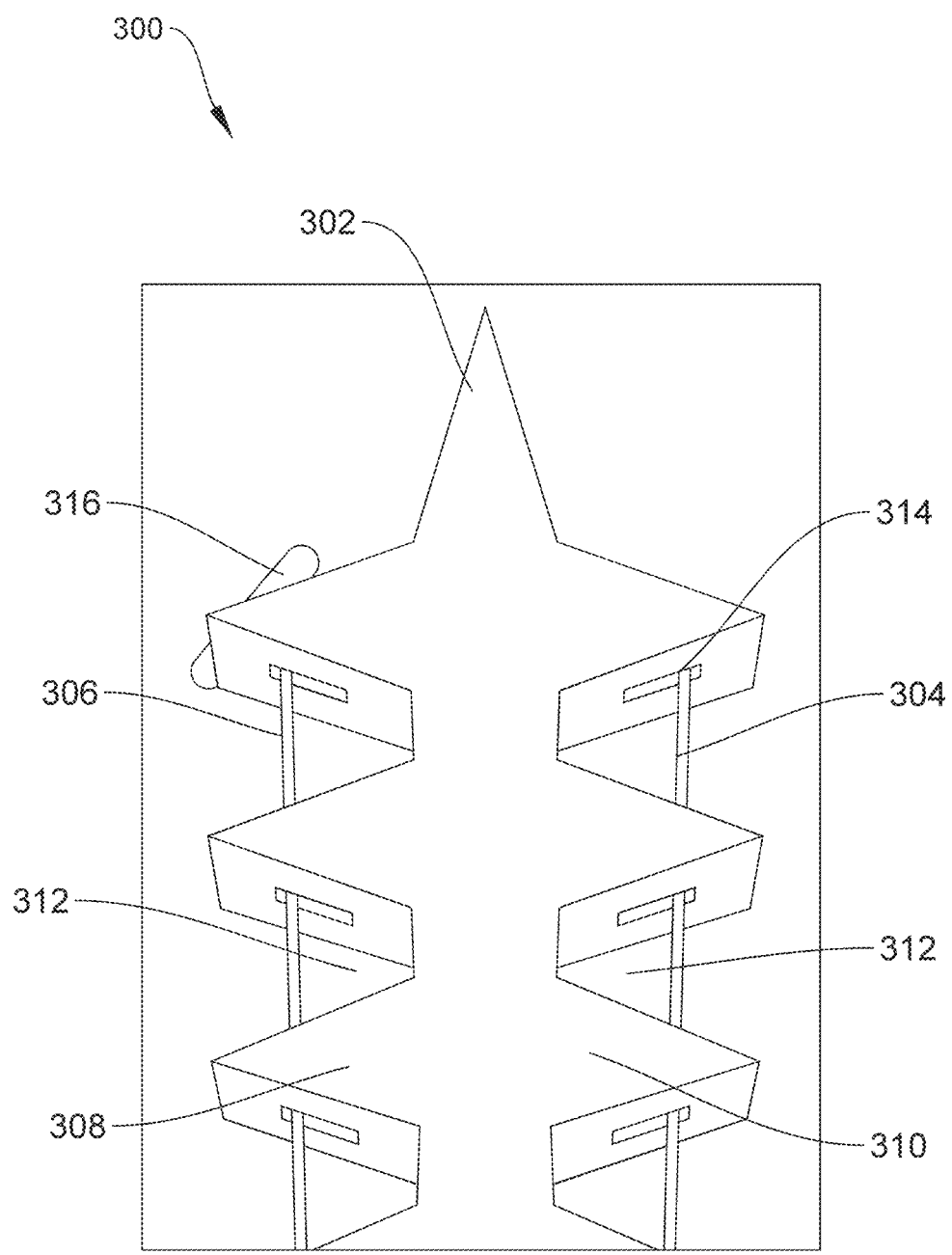
FIG. 4 illustrates an exemplary cable and tension system for flexing an actuator.

Design process: The overview of design process, and the components of the user interface system are demonstrated in FIG. 3. A Stewart mechanism is chosen as a joystick since it has 6 DOF and acts as a twin system for the soft robot. The kinematics of the Stewart mechanism may be used to obtain its size based on the required workspace. Next, the structure of the mechanism can be 3D printed and assembled. Linear potentiometers may be mounted on each leg of the Stewart mechanism (i.e., each actuator) so that it can sense its displacement. These mounted potentiometers may translate the sonographer's hand motion to the equivalent motion in the passive legs which must be mapped to the required bending motions in the active links of the soft robot. This mapping may be done through a calibration and a nonlinear mapping based on the bending profile of the soft robots' legs. Finally, this data may be used as a desired input motion of the soft robot. The position of the robot may be sensed by an electromagnetic (EM) tracker attached to the robot end-effector which may be mapped to the equivalent bending deformation of the robot legs through the kinematics model and feedback to the controller (FIG. 3).

Evaluation of design objectives: To validate the performance of the joystick, it may be moved and rotated in all 6 DOF to confirm that the soft robot performs accordingly. Performance may be verified optically, and/or through the collected data from EM tracker. A Matlab program may be utilized to generate the desired 3D trajectories within the robot workspace. The program may be configured to read and plot the sensory data of the robot end-effector position online. Next, the operator may use the joystick to move the robot and follow the desired trajectory by looking at a computer monitor.

In an alternative embodiment, soft pneumatic actuators may be used in place of soft tendon driven actuators.

To design a robust controller using the QFT method, the desired system specifications such as tracking and stability may be translated into robust performance bounds that consider the uncertainty. The robust performance bounds may suggest a very high gain for the controller that results in saturation of the actuator. To solve this, the tracking bounds may be modified by adding one zero to the upper bound and one pole to the lower bound at high frequencies. Robust control effort bounds may be introduced to limit the cost of feedback at the design frequencies and to ensure that the robust controller does not wear out the actuator.

First Example Demonstration Unit

Figure 5:
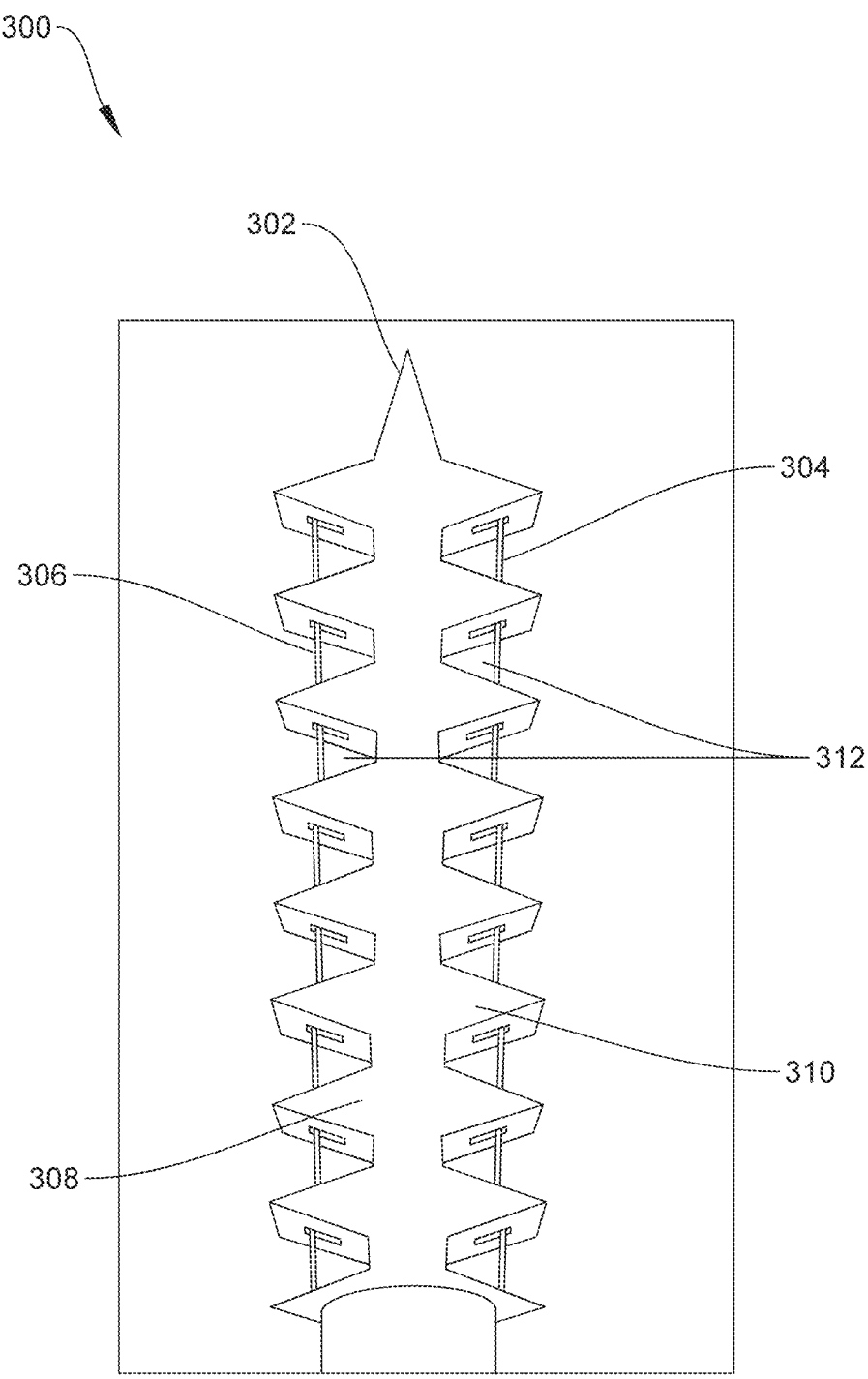
FIG. 5 illustrates an exemplary cable and tension system for flexing an actuator.
Figure 6:
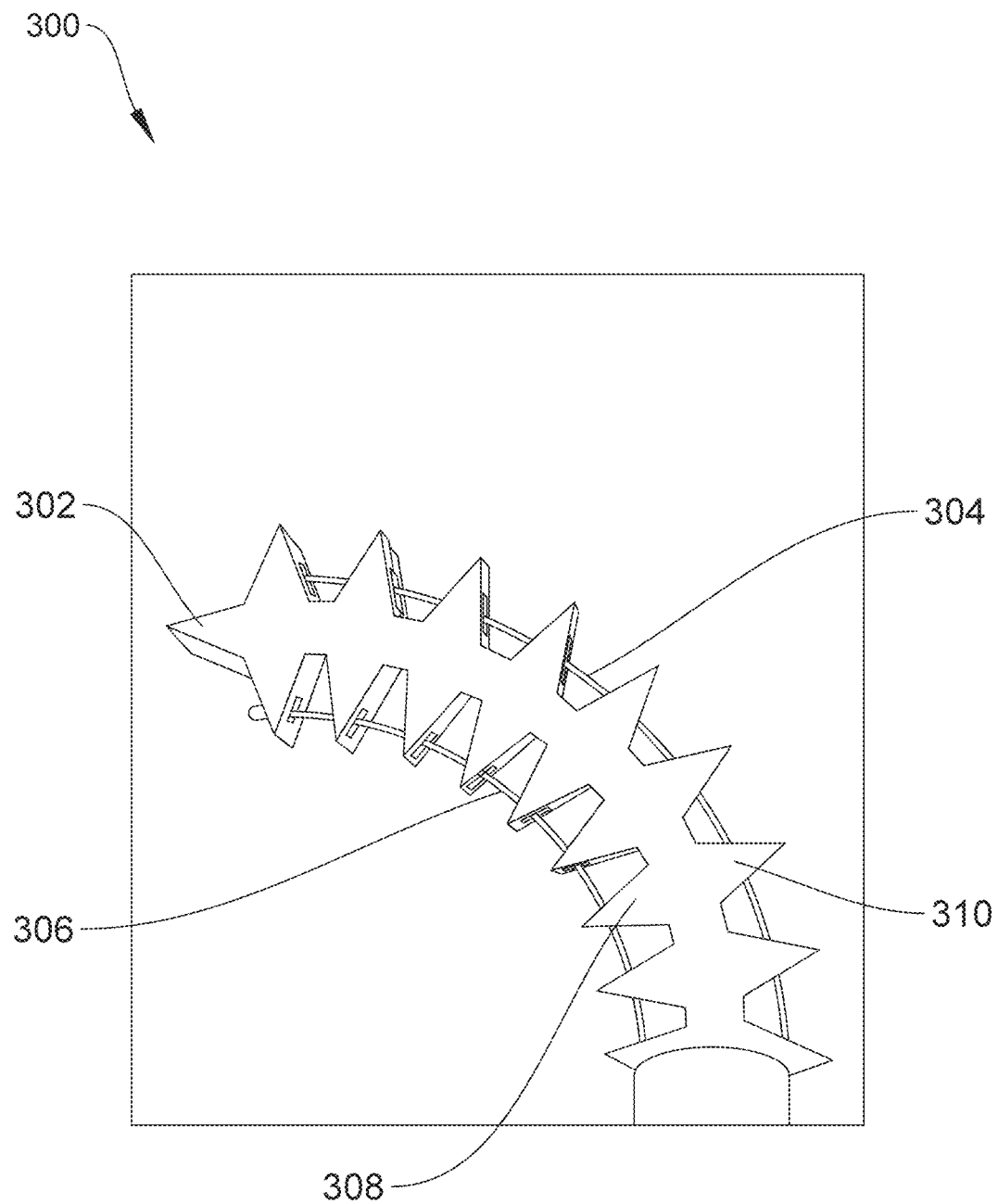
FIG. 6 illustrates an exemplary actuator flexed to the left.
Figure 7:
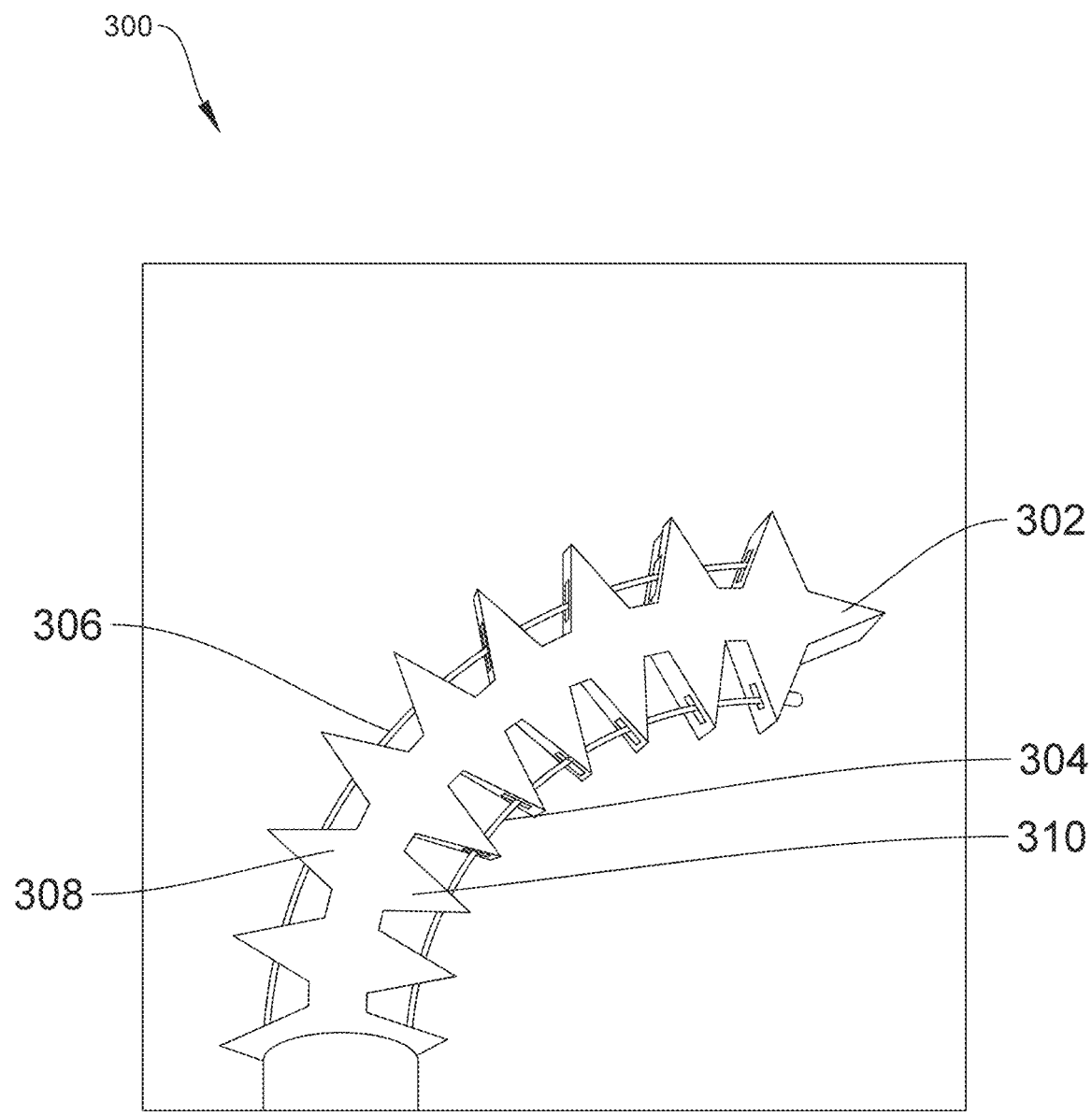
FIG. 7 illustrates an exemplary actuator flexed to the right.

The exemplary flexible link depicted in FIGS. 4-7 consisted of 8 fins with a length of 110 mm and an overall width of 26 mm. This flexible link may also be described as a tendon-actuated flexible link. These figures show examples of a flexible link 300 according to the present disclosure. The tip 302 of a flexible link is shown along with left side ridges 308 and right side ridges 310. These ridges 308, 310 leave spaces 312 for flexing on both sides. In each ridge 308, 310 may be a hole 314 through which may be threaded a cable or fiber 304, 306. The flexible link 300 has a left side cable 306 and a right side cable 304. For this proof of concept model, the left side cable 306 terminates at the top-most ridge with a nut or block 316 to prevent it from sliding out. A similar block exists on the right side (not shown in the figures). Alternatively, the left cable 306 and the right cable 304 may be joined or otherwise affixed atop this flexible link 300. FIG. 5 shows the full flexible link 300 when no tension is applied to the cables 306, 304 or when the tension may be roughly equal between the cables. In this example there are 8 fins 308, 310 on either side of the joint. FIG. 6 shows the flexible link 300 when more tension is applied to the left cable 306 than to the right cable 304. The left side ridges 308 may be drawn closer to each other into the spaces 312. The right side ridges 310 become further separated. FIG. 7 shows the same effect but with tension applied to the right cable 304 rather than to the left cable 306. Such a joint 300 may be fabricated by various means and operates as a tendon joint.

Thus, the fin-like ridges permit the soft link to deform in either direction once the string was actuated as shown in FIGS. 6 and 7. When the string running on both sides of the soft link was pulled/actuated on the left and released on the right, the link deformed to the left (see FIG. 6) Likewise, once the right string was actuated and the left string was released, the soft link deformed to the right as expected (see FIG. 7). Besides, the fins on the soft link prevented the pulling of the soft link more than a certain degree.

An initial soft robot was designed incorporating three such flexible links. These flexible/controllable arms were 3D-printed using thermoplastic polyurethane (TPU) and included a bottom portion with an active soft link and an upper portion with a compliant (semi-rigid) four-bar passive linkage as depicted in FIG. 1.

FIG. 1 illustrates a design of an arm/limb 700. The arm 700 comprises a passive upper portion 704 along with an active lower portion 702. The top 706 of the arm has a clip or location for affixing a platform, an end-effector, or an ultrasound unit. The arm in this example was connected to a base plate through the active soft link 702 with 10 mm thickness to create relative motion between each.

FIG. 1 shows a robot with six arms and 6 DOF. This example may otherwise be similar to a Stewart mechanism or the 3USR robot, but fabricated with soft arms. The mobile platform 802 may be connected to the lower platform 808 by six arms 700. Motors may rotate to apply tension to the cables which control the flexible portions 702 of the arms 700. A hinge or joint 810 may connect the portion of the arm which is flexible/actively controllable 702 with the passive, upper portion of the arm 704, upon which the upper platform 802 rests. In addition to the elements from FIG. 1, control electronics and/or a joystick (not shown) for controlling the upper platform may also be employed. In this disclosure the movable platform may be on the upper side or on the lower side.

An initial prototype soft delta robot 800 was fabricated. It consisted of three arms 700 with flexible and controllable flexible links 702 on the one portion of the arm and a passive semi-rigid part 704 on the lower portion of the arm. At the distal end of the passive part of the arm is a mobile platform 802 affixed by a top joint 706. Three servo motors (not shown) control strings to actuate the controllable flexible links 702 of the arms 700. A bottom platform 808 provides a base and also may house the servo motors and the control electronics. The flexible links 702 were 3D-printed using TPU and the mobile platform 802 and the fixed base 808 (which houses the servos in this example) were 3D-printed out of polylactic acid (PLA). In this embodiment, the flexible portions 702 of the arms 700 were attached on the base 808 spaced 120° apart from each other as well as apart from the center of the bottom platform. Also, the arms 700 were connected to the mobile platform 802 which was kept parallel to the fixed platform in its initial configuration. Each of the flexible portions 702 of the arms 700 had embedded strings that were actuated by a pulley wheels connected to the servo motors. The servo motors were connected to an Arduino for ease of control but can be controlled independently via a joystick or a computer.

If all the flexible soft links 702 of the arms 700 are actuated in the same direction, then the mobile platform 802 follows a straight up and down motion remaining parallel to the fixed plate 808. In an initial test, even though the mobile platform 802 was displaced due to the outward deflection of the active soft links 702, the displacement wasn't significant since the string loosened after several cycles due to the connections at the top end of the fin-like structure and the lack of tension. In addition, the passive portions 704 of the arms 700 were too stiff which prevented the required side to side motion. Consequently, the flexible links 702 bent side-to-side as opposed to bending along the direction in which the strings are actuated.

To address these issues, the initial design was modified. Taking into consideration the lack of tension in the strings as well as the flexibility and stiffness, the passive, semi-rigid portion 704 of the arms 700 were revised from having sharp corners to having curved corners with a smaller thickness. Besides, the flexible link thicknesses were increased from 10 mm to 14 mm to prevent excessive bending in the wrong direction(s). Also, in order to resolve the lack of tension in the strings, a pulley wheel was designed to tighten the string to the servo motor as well as incorporating a spring attached to both of the strings on each tendon—analogous to right side string 304 and right side string 306 from FIGS. 4-7. This attached spring allowed the servo-motor to pull the string more effectively while maintaining the proper amount of tension. In addition, the connection of the strings at the top ends of the flexible links 702 was changed from a permanent connection to an adjustable connection via a bolt and a nut. The bolt and the nut wrapped by the string added more tension to the string while allowing it to be adjusted whenever it became loose under actuation. After making the necessary adjustment to the soft delta robot, it was reassembled with the modified arms and the pulley wheels. Additionally, the mechanism was controlled by programming via the computer instead of manually by a joystick.

Figure 9:
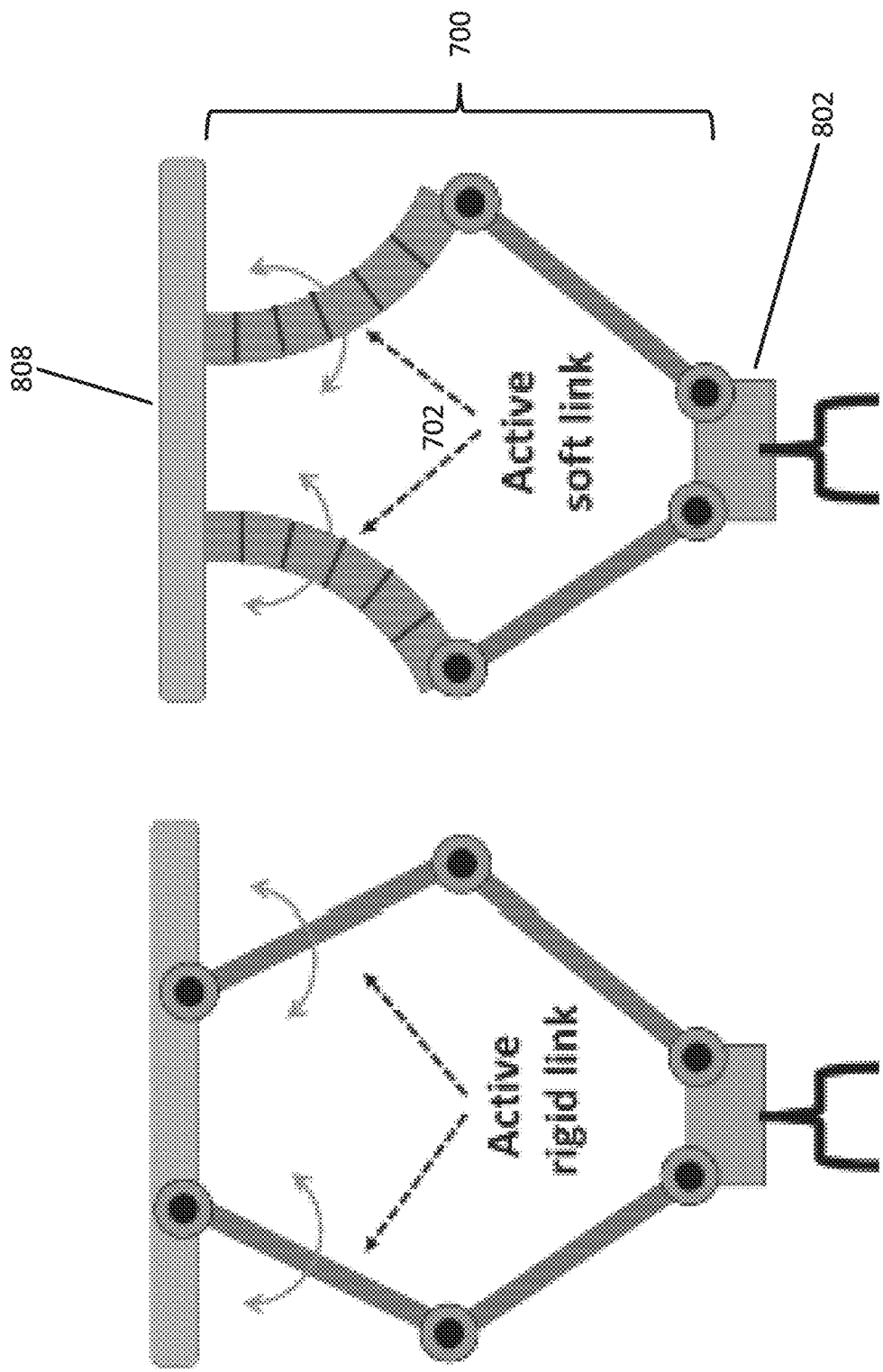
FIG. 9 illustrates a rigid parallel robot (on left) and a soft parallel robot (on right).

The soft delta robot experiment setup consisted of the soft delta robot 800, a power supply to actuate the motors, a laptop with MATLAB and Arduino Integrated Development Environment (IDE), and an ultrasonic sensor with its own Arduino control electronics. The upper platform 802 of the soft delta robot 800 was tested for up and down and side to side motion to ensure that the upper platform 802 remained parallel to the bottom platform 808 as well as testing the performance and behavior of the flexible links 702. A sensor was used to measure the distance at which the upper platform moved down. It was observed that the upper platform, as the soft links moved outward, was displaced by in the z direction. Different embodiments of this type of soft robot are depicted in FIG. 1 and FIG. 9. For example, FIG. 1 shows the movable platform being raised while remaining parallel to the fixed base (the top platform).

Modeling of Prototype Unit

A kinematic and dynamic model of the first prototype of the soft robot was developed using Matlab Simscape. Although soft robots provide more advantages compared to rigid mechanisms, their modeling is much more complex since soft link deformations yield nonlinear equations. Several approaches have been adopted in the literature. While the Cosserat rod theory may be used for the modeling of tendon-driven soft robots, modeling through finite element analysis is the most common method among many since it provides an accurate solution considering the material non-linearity.

In the exemplary design, each kinematic chain connecting the top plate to the support base is designed as an arm connecting to a base plate through a compliant four-bar linkage, a soft joint, and a flexible link. The deformation of the links is obtained from the kinematic model. Dynamical modeling can be achieved through the use of the Simscape model.

Kinematic Model

To develop the kinematics model of the soft robot, a constant curvature for the motion of the 3D printed tendon-driven actuators is assumed. Next, proper frames will be assigned to the soft robot platforms. Analogous to FIG. 8, the kinematics model of a three arm soft robot can be defined as follows:

$$\{B_i^B\}+\{L_i^B\}+\{l_i^B\}=\{P_p^B\}+[R_p^B]\{P_i^P\} \quad (1)$$

i=1, 2, 3.

where $\{B_i^B\}$ is the position of the vertex of the fixed platform for the robot and $\{L_i^B\}$ is the position of the soft actuators, where $\{l_i^B\}$ is the position of the passive links, $\{P_p^B\}$ is the position of the end-effector, $[R_p^B]$ is the rotation matrix, and $\{P_i^P\}$ is the position of the vertex of moving platform. Equation (2) states that the length of the passive links must be constant and equal to 1 such that $$l_i=\|l_i^B\|=\|\{P_p^B\}+[R_p^B]\{P_i^P\}-\{B_i^B\}-\{L_i^B\}\| \quad (2)$$

i=1, 2, 3

To avoid the square-root in the norms of the Eqn. 2, the equation is squared to get:

$$l_i^2=\|l_i^B\|^2=l_{ix}^2+l_{iy}^2+l_{iy}^2 \quad (3)$$

i=1, 2, 3

Equation (3) can be solved numerically to obtain the value of the required bending angle in the active links for a given position of the robot end-effector. To demonstrate the application of the kinematic model, both vertical and circular trajectories have been simulated.

Simscape Model

The proposed improved design consists of three main parts: a base 808, arms 700, and a movable plate 802. Once a new Simscape model is created using the command smnew, the blank model opens a default window with the world frame, solver, and mechanism configuration blocks. The gravitational force can be modified using the mechanism configuration block depending on the configuration of the design. A general flexible block was selected from the Simulink library to connect these three blocks. For this exemplary model, the soft link arms were assigned four sections. The bottom of the arm connected to the base is a compliant flexure with a height of 90.5 mm and a thickness of 6 mm. Nine protruding triangular ridges on both sides of the compliant flexure (the flexible section of the arm) permit this bottom portion of the arm to bend inwards and outwards. There is a small opening down the face of all ridges where a cable will pass through to deform the soft links. Two cables are connected to the top ridge to bend the soft links in two directions through the servo motors. This arrangement allows both inward and outward movements depending on which cable is pulled down. The exemplary arm consists of soft and compliant links which have a height of 120 mm and a width of 1.5 mm possessing flexure hinges at the edges. The compliant flexures allow the links to bend and revolve depending on the actuation. For simplicity, the protruding triangular regions are omitted in the Simscape model. Rigid Transform blocks are used to position the placements of the cable while a brick solid block is connected to the top of the general flexible block that will be used to tie the ends of the cable. This brick solid block has the same distance across the small holes in the arm's first region ridges and to connect the cable to the brick solid ends, frames are introduced in the settings of the brick solid block. A belt-cable end block is used to attach the cable to this frame. For the first test, the top cable on both sides of the brick solid was pulled down. To model the pulley mechanism, the belt-cable end is connected to a pulley block located at the bottom of the general flexible block. The bottom pulley is located at a distance by using a rigid transform block. The rigid transform block is connected to a revolute joint to rotate the pulley along with a cylindrical solid that must be used for the pulley wheel. The revolute joint and the cylindrical solid are also connected to a belt-cable spool which represents the pulley. A torque is applied to the revolute joint to pull the cable.

The basic idea in modeling the active soft links is to consider them as a discretized system which consists of rigid finite elements (RFEs) connected by spring-damping elements (SDEs). Once the simulation results were confirmed with the experimental setup, the soft links were integrated into the rest of the mechanism. Four revolute joints are utilized to imitate the compliant flexures on each passive links. To this end, each of the active soft links is modeled using four segments connected through serial revolute joints and connected to the pulley. The passive soft links are also joined to the passive compliant links thereby increased the simulation time. To address this problem, a general flexible beam with TPU properties is replaced with a segmented link connected via revolute joints with the spring value K having the same load-deflection behavior as the general flexible block. This method not only enabled faster simulation response but also increased the accuracy of the dynamic solution.

In a demonstration, the strings were actuated by motors and displaced the movable top plate by ~12 cm. The strings may be pulled to produce many possible displacements and orientations of the soft robot. The superiority of the Simscape modeling of soft robots is that any data can be exported if the corresponding sensors are utilized in the model.

Although the simulation time would significantly be affected, as an alternative to the creation of the design using the Simulink library blocks, a CAD model of the mechanism can be imported into Simscape and the soft links and flexures can be replaced with the flexible beams and torsional springs. The compliant four-bar linkage can also be modeled using pseudo-rigid body modeling by replacing each flexure with its equivalent torsional stiffness having the same load-deflection behavior.

Second Example Demo Unit (Six Arm Unit)

The design of the soft robot is inspired from the structure of a rigid Stewart mechanism. To transform this mechanism to its analogous soft robot the linear actuators and rigid joints are replaced with passive links, flexible links/soft bending actuators and soft joints. This design consists of the following: six arms (each arm comprising two soft joints, a passive link, and a flexible link), six servo motors and mounts, six wire wheels, a mobile platform and modular base assembly.

In the example shown in FIG. 1, each of the six soft closed kinematic chains (arms/limbs 700) consists of one passive link 704, one flexible link 702 (e.g., soft tendon-driven actuator), and two soft joints (a first soft joint 810 between the flexible link and the passive link and a second soft joint 706 between the passive link and the mobile platform). The example full soft robot 800 further includes a movable/mobile platform 802, and a base or fixed platform 808. In the embodiment shown, the flexible links 702 at the ends of the arms 700 are attached to the base platform 808 with a 4 mm bolt through a hole in the end of the soft link, and the passive link 704 is attached permanently to the underside of the mobile plate 802 by a soft joint 706. The six arms are grouped in pairs and the pairs are orientated 120 degrees from the other paired arms. Within each pair of arms, the arms are spaced 30 degrees apart. Other arrangements with more or fewer limbs are also possible.

The soft joint design for this prototype was chosen over a standard ball and socket because the latter would have to be made with a rigid material and would wear over time. Of the many joint designs considered, the hyperbolic profile has been shown to provide the most stable point of rotation. After 3D printing and testing several diameters, the current diameter of 2.8 mm was the dimension that showed to be effectively durable and flexible.

Additionally, the soft tendon driven actuators are designed to have thread run along the length of the part. This thread is responsible for the link's motion (CW and CCW rotations); when the thread is pulled on side, the link will flex towards that pull. This actuation is controlled with the rotational motion a wire wheel that is connected the threads to Arduino-type control circuits that controlled by a computer program.

This forward and backward actuation is achieved by the rotation of a servo motor that is connected to a wire wheel where the threads tie in. The servo's motion is controlled via computer is an Arduino IDE.

In an embodiment to make the design modular and simpler to 3D print, the base assembly may be split into a base top, base bottom, and connecting legs which may be bolted together with metric screws and bolts (or may be otherwise connected). The soft link and compliant flexure links are printed with Ninjaflex using 100% infill. This material was chosen for its Shore hardness (85A) and stretch/elongation (660%) which allowed for maximum flexibility while retaining enough stiffness for the build to remain upright independent of other support. In an example, the entire base assembly, top plate, all wire wheels, and compliant links were 3D printed in polylactic acid (PLA), but other materials may also be employed.

In an initial prototype demonstration unit, the thread that actuated the soft links was secured with a nut and bolt to allow for retightening after each experiment. However, the nut and bolt did not hold together well after several actuations and would occasionally shoot off the threads when the link was actuated aggressively enough. A new design based on a boat cleat was created and 3D-printed and improved the situation. The resulting solution held firmly through the experimental runs while still allowing for easy disassembly.

Individually, the soft links are each capable of a single degree of freedom (1 DOF) motion as described earlier. However, when the model is completely assembled, the soft link and joint design allows for complete 6 DOF motion of the upper platform.

As shown in the right hand side of FIG. 1, when the soft links 702 are actuated outward, the movable platform 802 is moved vertically. Vertical displacement can be achieved by flexing the active soft links 702 away from the center of the base plate 808. (In principle, flexing the active soft links 702 towards the center of the base plate 808 may also cause vertical displacement for the mobile platform 802, but this instance is not illustrated in these figures.) The vertical displacement of the movable platform 802 is more significant with outward actuation (e.g., by applying more tension to the outer strings on all the soft actuators/soft links 702). Horizontal motion with some tilt can be achieved by flexing a single pair of links at a time, while tilting of the upper platform or rotation of the upper plate, including roll, pitch, and yaw, may be achieved through various combinations of active flexible links 702.

An exemplary soft robot experiment setup consists of the demonstration soft robot, a power supply, a laptop with MATLAB and Arduino IDE for control, a 6 DOF electromagnetic sensor (e.g., a motion sensor or a position sensor), an electromagnetic transmitter, and the sensor electronics unit. To experimentally validate that the robot has 6 DOF and is capable of moving in arbitrary points within its workspace, the position and orientation of the robot will be sensed by an electromagnetic (EM) tracker attached to the robot end-effector (in this instance the upper platform). Similar EM trackers have been successfully used in other studies to measure the 6 DOF motion. The exemplary system consists of two main components: a sensor and an EM transmitter. Additional sensors provided additional accuracy for the measurement. The sensors are arrays of small coils which may be placed at, for example, a catheter tip or at various positions on the movable top plate. The transmitter generates a small EM field which the sensors detect. The motion of the sensors is determined by the detected strength of the EM field. The system is capable of measuring 6 DOF motion (motion over x, y, and z, and rotation for roll, pitch, and yaw).

Kinematic Model

Figure 8:
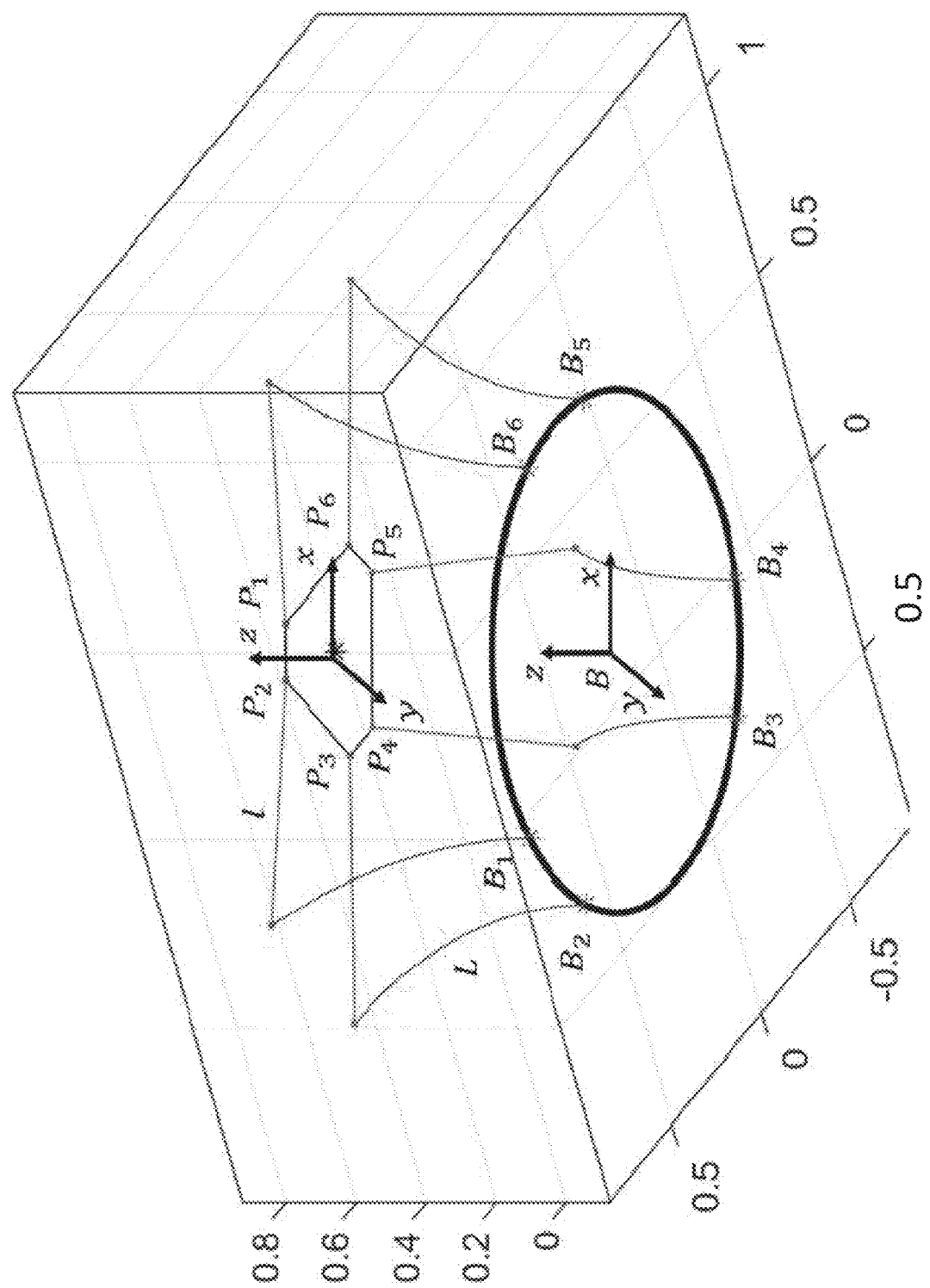
FIG. 8 illustrates a coordinate framework for modelling the motion of a soft robot.

As noted previously a constant curvature may be assumed for the motion of the 3D printed tendon-driven actuators. Next, proper frames are assigned to the soft robot platforms. FIG. 8 illustrates the kinematics model of the 6-limb (6-arm) soft robot which can be defined as follows:

$$\{B_i^B\}+\{L_i^B\}+\{l_i^B\}=\{P_p^B\}+[R_p^B]\{P_i^p\} \quad (4)$$

i=1 to 6.

Just as in equation (1) above, these terms have their same meanings, except that now the indices run from 1 to 6 instead of 1 to 3 to account for the additional arms. For reference the definitions are repeated here. $\{B_i^B\}$ is the position of the vertex of the fixed platform for the robot and $\{L_i^B\}$ is the position of the soft actuators, where $\{l_i^B\}$ is the position of the passive links, $\{P_p^B\}$ is the position of the end-effector, $[R_p^B]$ is the rotation matrix, and $\{P_i^p\}$ is the position of the vertex of moving platform. The length of the passive links must be constant and equal to 1 such that $$l_i=\|l_i^B\|=\|\{P_p^B\}+[R_p^B]\{P_i^B\}-\{B_i^B\}-\{L_i^B\}\| \quad (5)$$

i=1 to 6

Equation (5) can be solved numerically to obtain the value of the required bending angle in the active links for a given position of the robot end-effector. To demonstrate the application of the kinematic model, trajectories may be simulated.

Simscape Model for Second Example

Despite the motion capabilities and superiorities of the compliant joints/mechanisms and soft robots, derivation of the mathematical model of complex designs including their dynamics is a very challenging task. A graphical user interface (GUI) was designed in Matlab Simscape for an exemplary 6 DOF soft robot comprising soft links, compliant spherical and large deflecting flexure hinges. Matlab Simscape enables the analysis of systems either by importing the CAD model or generating the models using the Simulink library. One of the salient features of Simscape modeling is that the simulation results can be exported to the workspace while 3D visualizing the motion through the mechanics explorer. Elsewhere in this disclosure the design and development of compliant mechanisms by 3D printing are discussed as well as the modelling of the same systems in Simscape to test how accurately Simscape models simulate a physical system.

The exemplary Simscape model of this robot consists of four main body parts: a bottom plate for housing the motors, rigid arms, a top plate, and soft links. Additional elements required to build the model include a subsystem of the spatial contact forces, transform sensors, and workspace blocks which collect the coordinates of the top plate. While the top and bottom plates are imported from Solidworks files using solid blocks, the soft links, the flexure hinges connecting the rigid arms to the top plate, and the compliant spherical joints connecting the soft links to the rigid arms are created using Simscape library blocks. First, a single arm is modeled by a soft link connected to a hinge with a spherical joint, and rigid arm with a spherical joint without a top connection. The soft link may be generated by utilizing the alternating extruded solid blocks and revolute joints. The cross-sections for the extruded solids may be created using the cross-section sketch of the SolidWorks part file. The stiffness of the soft link may be adjusted through the spring stiffness and damping coefficient properties of the revolute joints. The tip of the soft link may be connected to a conical hinge. In this example, the physical hinge used in the experimental model resembles a spherical joint. In the example Simscape model, the hinge may be created by first splitting the hinge into two while connecting the two pieces together using a spherical joint block. The stiffness of these joints may be tuned from the internal mechanics of the spherical joint block. In an example, a cylindrical solid with a radius of 5 mm and length of 96.3 mm may be connected to the hinges. The free end of the soft link may be connected to the bottom plate and the top of the second hinge may be connected to the top plate.

Since the physical setup of this exemplary demonstration 6 DOF soft robot was tendon-driven using the servo motors applying tension via pulleys to bend the soft links either inward or outward, a similar structure may be employed in the model. In the model, the cylindrical solids were connected to the belt-cable spool block to simulate the servomotor(s). A smaller cylindrical solid is placed within each extruded solid element at the point where the string runs through the physical model. Each of these small cylindrical solids may be connected to revolute joints and pulley blocks. This series of pulleys ends with a belt-cable end block at the last element of the link. It should be noted that belt-cable properties block must be connected to the pulley system. The revolute joint that is connected to the motor cylindrical solid is actuated using a motion input and a position sensor is set to collect the rotation data of the motor. This pulley system replicates the strings used to pull the links in the physical model. Spatial contact force blocks are applied between the rigid cylindrical solids of each arm to prevent penetration between the arms. In some embodiments, there are a total of 15 spatial contact force blocks used to establish contact from arm to arm.

A GUI may be used to enter parameters for controlling the soft robot. Once the user double clicks on the image, the App allows the user to enter the material properties of the soft link and change the input angles. The user can also open the Simscape model by simply clicking on the little arrow on the bottom left corner of the image and change the geometry of the soft and rigid links. The mobile plate trajectory depends on how (inward/outward) and how many soft links are actuated.

Model Validation

The coordinates of the top plate were recorded using the 6 DOF sensor from the experimental setup while bending all soft links through the pulleys and the servo motors by 35° in the outward direction. Same inputs are supplied to the Simscape model. Small deviations between the experimental and modelled displacement may occur due to the delay in the actuation of the motors through Arduino and the adjustment of the string tension of each soft link. Overall, the simulation and the experimental results are largely in agreement with and thus validating the Simscape model.

Design Considerations for a Hybrid Cable-Driven Soft Robot

Figure 10:
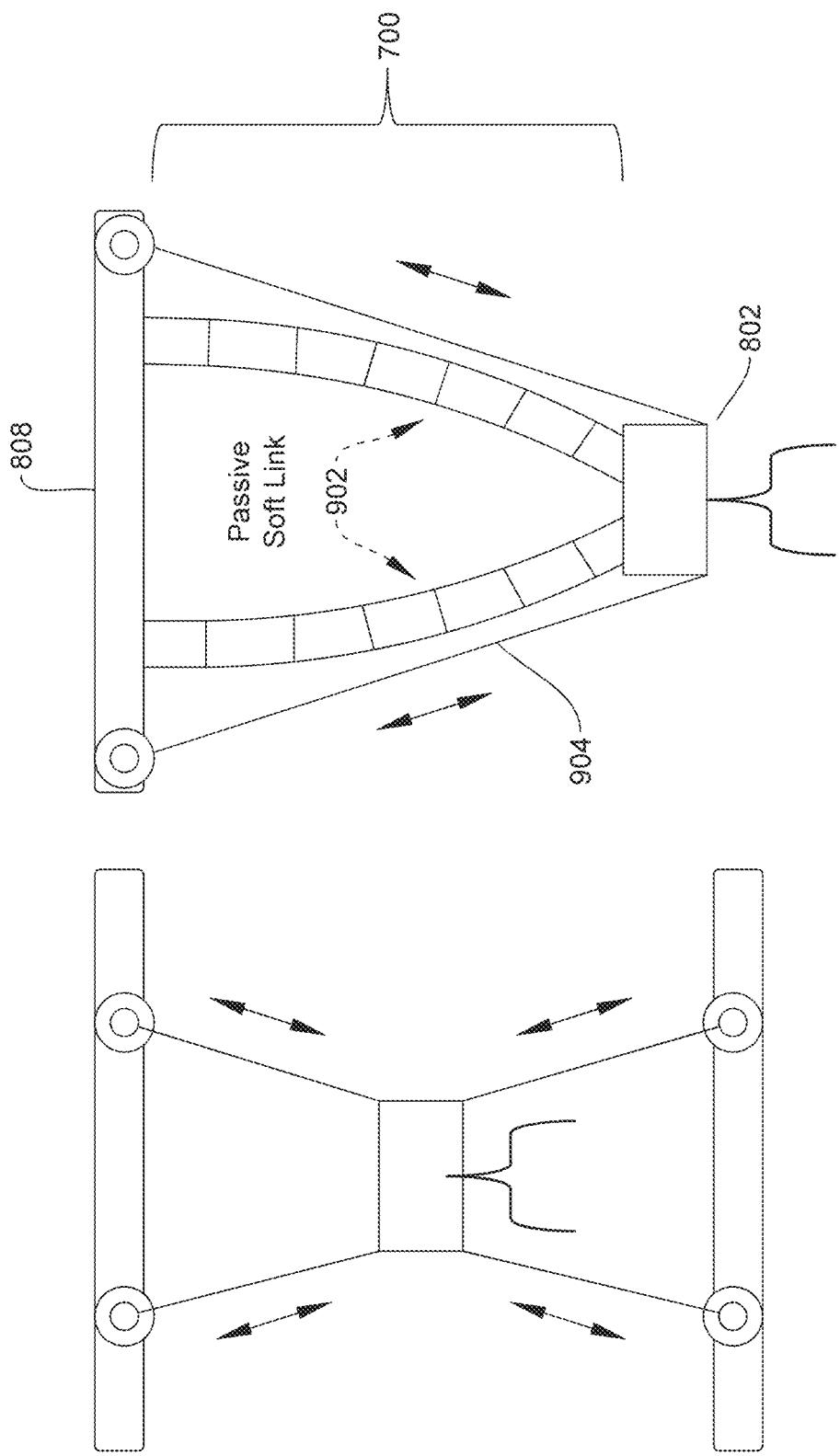
FIG. 10 illustrates a cable-driven parallel robot (on left) and a hybrid soft cable-driven parallel robot (on right).
Figure 11:
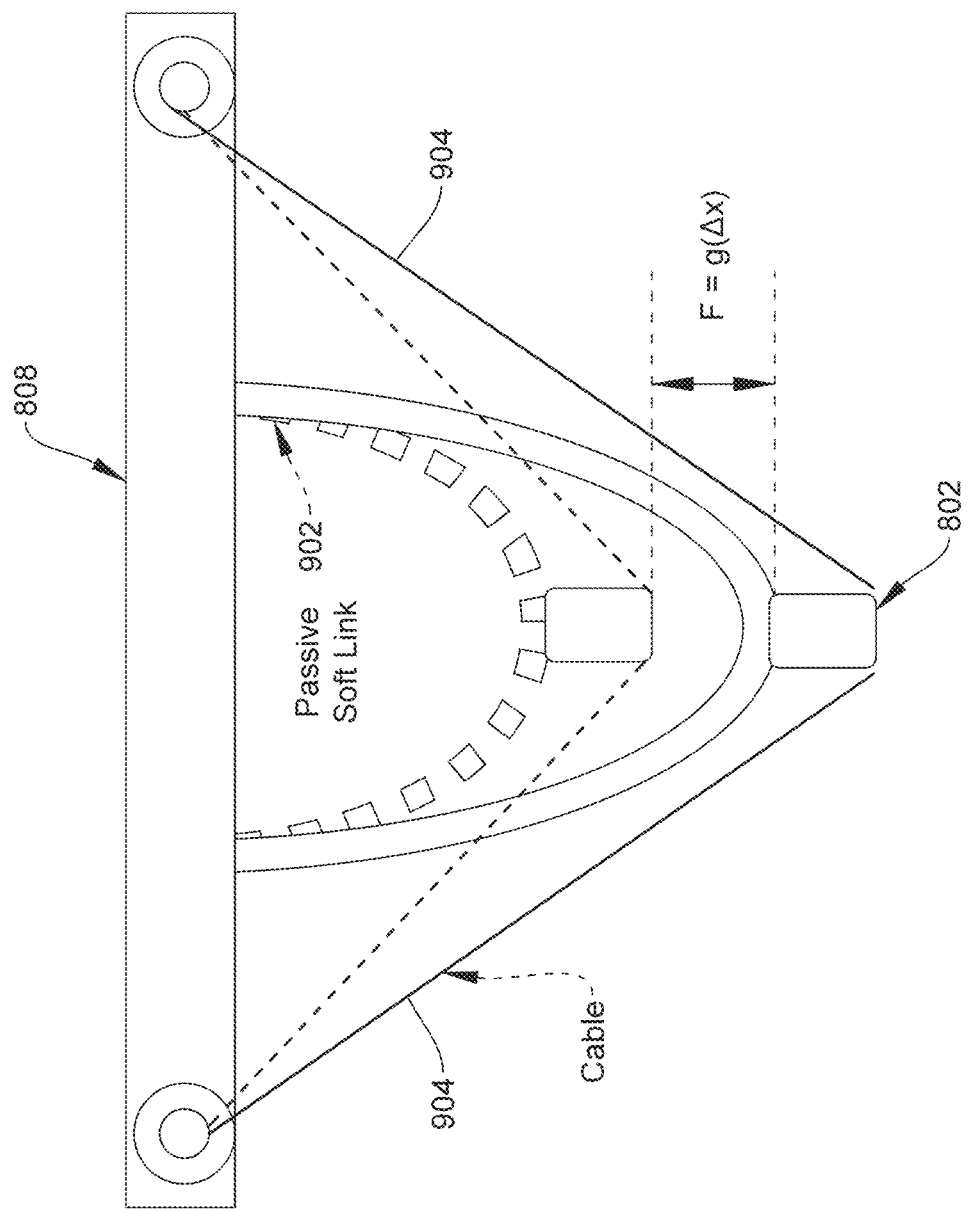
FIG. 11 illustrates the interaction of a passive soft link with a cable and pulley system to provide tension.

This section discusses the design and fabrication of the remote ultrasound soft robot and demonstrates the experimental results. In the first part, the concept of hybrid soft cable-driven parallel (HSCP) robots will be discussed. Next, the designed objective for the soft ultrasound robot will be detailed, and finally, the design and fabrication of the soft robot prototype will be presented. As illustrated in FIGS. 9-11, soft robots can be designed by replacing the rigid links and joints in the structure of a rigid parallel robot (left side of FIG. 9) or of a soft parallel robot with soft links (right side of FIG. 9) and joints. The addition of active soft links 702 to the structure of soft parallel robots provides an extra design feature to adjust the overall stiffness of the robot. By engineering the stiffness of the robot, the safety of human-robot interactions can be improved. In the design of soft parallel robots, typically soft active links 702 transfer the desired motion to the robot end-effector (e.g. the mobile platform 802). Considering the complex, nonlinear deformation of soft links, the modeling and control of soft parallel robots can be challenging. Alternatively, as shown in FIG. 10, the motion to the end-effector can be directly transferred using cable-driven actuators (FIG. 10, left side) or cables 904 combined with passive soft links 902 (FIG. 10, right side) may control the position and orientation of the movable platform 802 relative to the fixed base 808. This new design, which combines cable-driven robots and soft robots has the potential to simplify the modeling and control of the soft robots.

To be the most useful for ultrasound (or other) applications, a soft robot must have 6 DOF (three translations, and three rotations), its workspace must cover an area of interest above the abdomen of the patient, and the overall stiffness of soft robot must be designed in a way that it can apply the required forces for proper ultrasound imaging and still be within the safe range for the patient. FIG. 2 and FIG. 11 illustrate the basic design strategy for a soft ultrasound robot. The structure of the soft robot can be considered as a nonlinear spring where the reaction force of the soft robot (F) is the function of robot displacement ($g(\Delta x)$). The complete design process may require several iterations to optimize the shape and number of the soft links for a given set of workspace and force constraints according to FIG. 2. In such cases, the design process can start based on the workspace constraint. In an example this constraint is the required area to be scanned on the patient body. This constraint defines the length of the soft links, the size of the base, the size of the top plate, and the distance required to move the upper platform. The constraints consequently may change the thickness and number of the soft links or their material parameters in order to satisfy the force constraint(s). In an embodiment, this force is the required force for ultrasound imaging. This process may be repeated several times to converge to an optimal solution. The demonstration robot achieved six DOF and its interaction force was relatively uniform within its workspace and was adjustable by changing the number of soft links used in the design.

Figure 12:
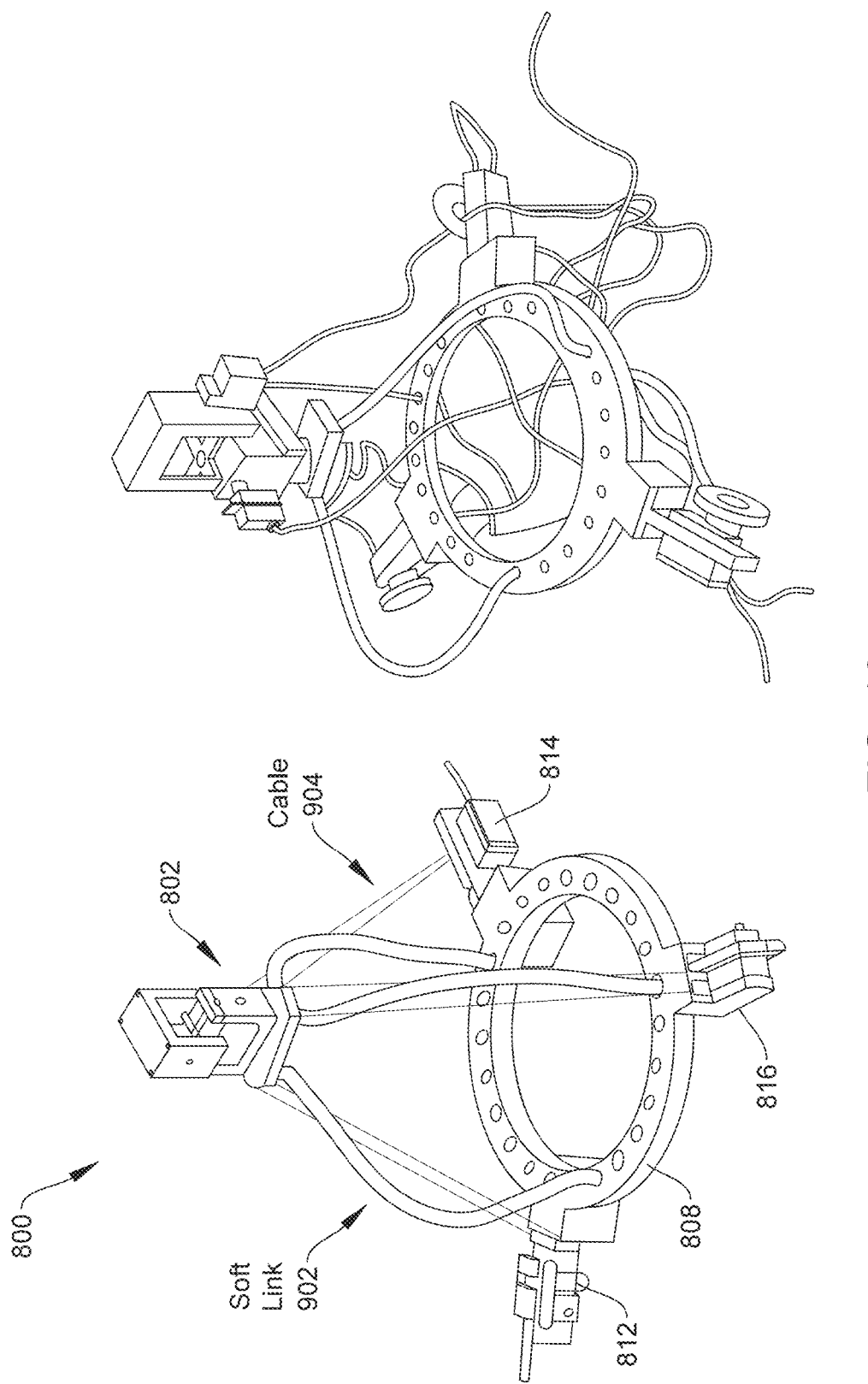
FIG. 12 illustrates a three-link design and a fabricated 3-link soft cable-driven robot.

To create a parallel robot with six DOF, the starting design point can be the structure of well-known Stewart mechanism. This mechanism consists of a fixed and a moving platform which are connected together through six linear actuators. To transform this mechanism to its equivalent hybrid soft cable-driven parallel robot, the six linear actuators can be replaced by six cable-driven actuators which connect the fixed platform to the moving platform through soft links. The initial experimental data demonstrated that while the Stewart mechanism design can effectively create three translational motions for the soft robot, it may fail to generate the required orientation for the robot. Thus, the initial design was modified to use only three cable driven actuators to create the required three translational motions and adding a three DOF wrist to the moving platform to accommodate the required orientation of the robot. These updated exemplary designs are displayed in FIG. 12 and FIG. 13. In an embodiment, the robot consists of a fixed platform 808 and a moving platform 802. In the example shown in FIGS. 12-13, the fixed platform 808 is the bottom platform and the moving platform 802 is the upper platform. In FIG. 1, the fixed base 808 is the upper platform and the mobile platform 802 is the lower plate. The two platforms are connected with three or more passive soft links 902 (e.g., 3 passive soft links (FIG. 12) or 6 passive soft links (FIG. 13)). Some designs added more soft links 902 to satisfy the force constraint, and more can be added as needed (e.g., FIG. 18). Three electromotors 812, 814, 816 spaced 120° apart actuate the moving platform 802 through a cable 904 and pulley mechanism for controlling the location of the mobile platform 802. This spacing of the motors & cables creates three translational motions. To generate three rotations a three DOF wrist mechanism can be added to the upper platform 802. In the example shown in FIG. 12 and FIG. 13, a wrist with only two rotations is shown.

In an embodiment, the fixed base is circular with 3 mounting plates around the outer diameter of the base. Each of the servos are placed at an angle of about 15 degrees from each of the two edge anchor points of the top (movable) platform and shifted about 4 cm clockwise around the base, to avoid slippage and provide accurate tension for the cables. The servos control the cable wound around the wire wheel and secured at the anchor points of the upper platform. The upper platform is also rigid to support the uniformity of the forces applied to the top section. In an example, the top section may hold a 9 g servo-motor that actuates a universal joint. The cables keep the links in tension and provide flexibility in complex environments for motion. The links are connected to the top plate and to the bottom base to keep a constant force when (generally nonlinear) actuation is applied.

Fourth Example: Universal Joint Design

A simple design to create a three DOF wrist may involve using a three perpendicular axis rotation by adding a yaw motion to a universal joint. In the example depicted the universal joint may comprise only two yokes and the yaw motion motor is not shown. In another example, the universal jointed comprises 3 parts: two yokes and a cross. One yoke and two opposite rods of the cross may contain a servo mount to hold the servo and produce the desired rotational motion when needed. Two rods are secured together with a screw to assemble a cross. An example universal joint (pictured in FIG. 14) may be controlled by two (e.g., 9 g) servos, with an additional servo in the slot of the upper platform to produce yaw movement (rotation about the central axis). The two remaining servos are attached, one at each opposite yoke to produce roll and pitch movements. FIG. 14a (left side) shows a CAD model of a universal joint soft and FIG. 14b (right side) shows the same joint along with the two attached servo-motors.

Fabrication

The printing parameters may be optimized to acquire the best results and save material. In an example, the remote ultrasound robot used common materials for 3D printers, such as polylactic acid (PLA) and Ninjaflex for simple and low-cost fabrication. The soft links, which are pliable and hexagonal shaped, may be printed with Ninja with 80% infill. Meanwhile, the base, upper platform, wire wheels, servo holders, servo mounts and the components of the universal joint, may all be produced using PLA and printed with 80% infill. The cross of the universal joint is printed separately into two rods for security and for simple assembly. One end of each rod is printed with servo mounts to produce the necessary movements, such as roll, pitch and yaw. The two yokes may be printed disjointly in two parts in polylactic acid (PLA) to secure the cross and the yokes.

Modeling and Control

During the kinematic modeling and the trajectory planning of the ultrasound robot, all code is executed in MATLAB or in the Arduino microcontroller. The kinematic model consists of two components. The first part is the model of the hybrid soft cable-driven robot which generates three translational motions in x, y, and z directions, and the second part of simulation uses the rotation matrix (Euler angles) to generate the orientation of the robot using the three DOF wrist.

Figure 15:
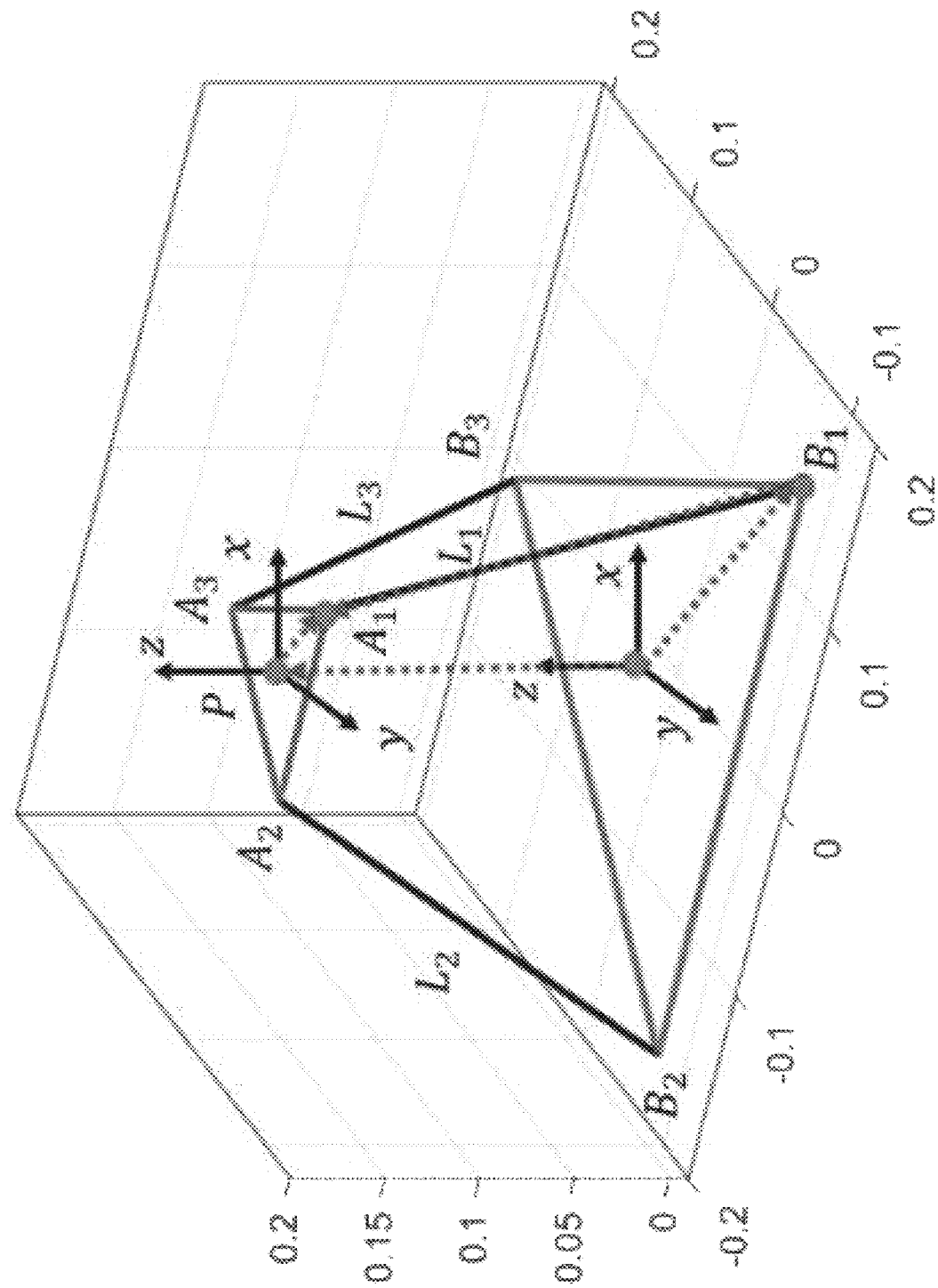
FIG. 15 illustrates frame assignment and coordinate system for the movable platform in Simscape for a soft link cable-driven robot with three cables.

In this example, the kinematics model of the hybrid cable-driven soft robot is developed assuming that the cables 904 are always in tension, due to the stiffness of soft passive links 902 (i.e. the passive links are in compression, trying to push the mobile platform 802 away from the base 808). In addition, for this example, the moving platform 802 (on top) remains parallel to the bottom (fixed) platform 808. A more generalized kinematics model is straightforward to implement. Next, proper frames are assigned to the soft robot platforms. Analogous to FIG. 8, FIG. 15 shows a kinematics model of the soft robot which can be defined as follows:

$$\{B_i^B\}+\{L_i^B\}=\{P_p^B\}+\{a_i^A\} \quad (6)$$

i=1, 2, 3.

where $\{B_i^B\}$ is the position of the vertex of the robot's fixed platform and $\{L_i^B\}$ is the position of the cables, $\{P_p^B\}$ is the position of the end-effector, $[a_i^A]$ is the position of the vertex of moving platform. In this example there are again only 3 arms, so that the indices run from 1 to 3. The rotational motion is achieved separately using the universal joint motors and the yaw motor. Alternatively, with additional cables, passive soft links, and motors more DOF can also be achieved.

Universal Joint Controls

Controls may be used to derive the desired trajectory of the universal joint as well as the servo inputs needed to complete these trajectories. The controls of the universal joint are straightforward, the user is able to input the movement that is desired in roll, pitch and yaw movements as well as how long the pattern should be actuated. The script then applies the movement pattern over the desired timeframe and finds the angle desired for each servo over the trajectory. The script then stores all of these angles in an array that is used later in the controls process. It is worth noting that the timeframe used in this script is often imported from the hybrid soft cable driven controls to ensure that the system actuates for the same amount of time across each of the six servos.

Communication and Control

Figure 16:
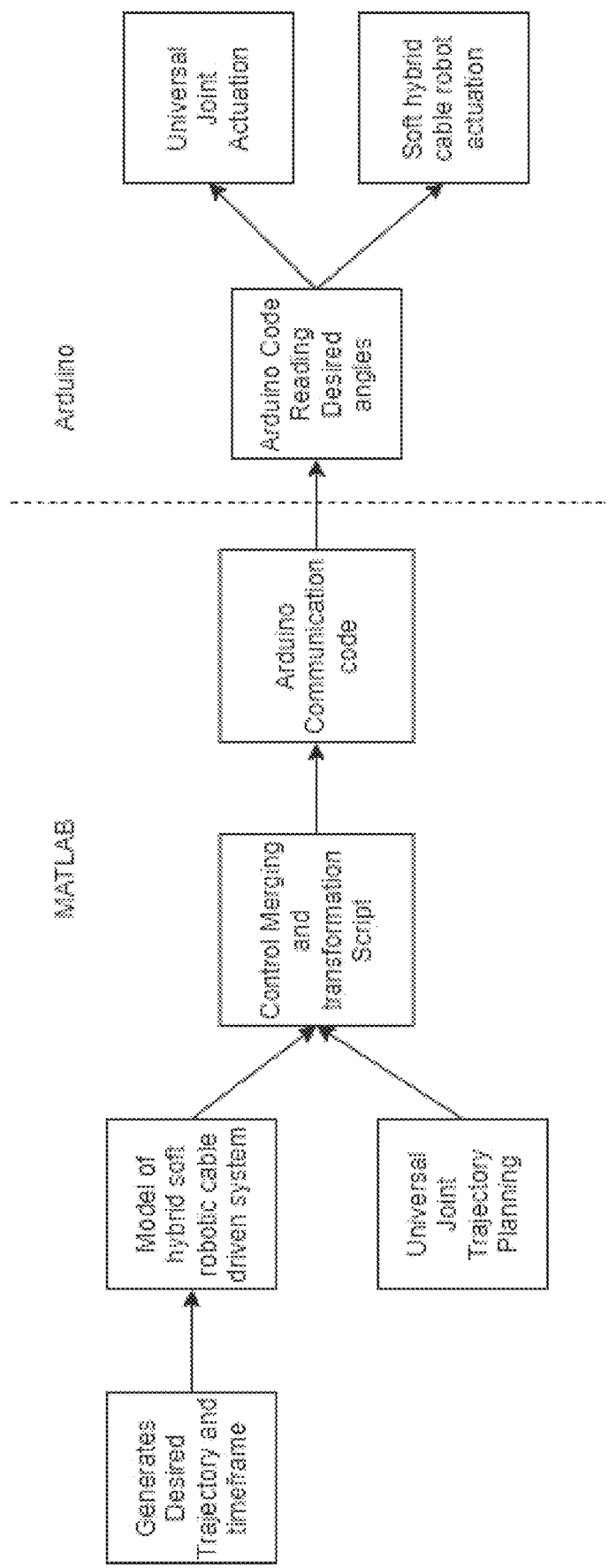
FIG. 16 illustrates a breakdown of exemplary control circuits.

An exemplary controls flow is detailed in FIG. 16. Methods according to embodiments of the disclosure include full controls flow as well as communication processes between the different scripts for generating the hybrid soft cable driven trajectory, the universal joint trajectory, and the Arduino microcontroller. The exemplary controls flow described in FIG. 16 is separated into two parts, MATLAB and Arduino. In an embodiment, the MATLAB controls flow goes as follows. The desired X, Y, Z, roll, pitch, yaw trajectories are input by the user into their respective scripts. From there the desired trajectory for the X, Y, and Z movement is given to the model of the hybrid soft robot system which outputs the changes in the lengths of the cables needed to complete the trajectory. The universal joint trajectory planning uses the rotational matrix of the robot to calculate the angles for each servo on the universal joint for each given point. These angles, as well as the changes in each cable length derived from the model of the hybrid soft cable driven system, are given to the control merging and transformation script which finds the angles of the bottom three servo motors required to actuate to the desired position and combines these angles with the universal joint controls into a single control matrix. This matrix is then given to the Arduino communication script which transmits the angles to the microcontroller which begins the Arduino controls flow. The Arduino receives the angles via serial communication from the laptop. It reads in the six desired angles simultaneously for each point in the trajectory. Then the microcontroller sends each desired angle to the servos in both the universal joint and to the servos in the baseplate of the hybrid soft cable driven system.

Validation and Demonstration

An exemplary setup was used to take all position setup as well as all roll, pitch and yaw data. This experimental setup consists of the ultrasound robot as well as an external power supply to support the six servos in the system. A laptop is used to connect to the Arduino microcontroller used in the ultrasound robot. This laptop runs the MATLAB scripts used to create the desired trajectories and send the desired angles to the ultrasound robot. The sensor electronics unit connects to the electromagnetic transmitter and the position sensor, which reads in its position compared to the transmitter. The position sensor is affixed to the top of the universal joint of the robot in order to properly measure the top plate's position data during the different trajectories tested.

An alternative embodiment was used to test the force profile of the soft robot. This experimental setup also contains the ultrasound robot system as well as an external power supply for the actuation of the servos in the system. A computer is attached to an Arduino microcontroller to control the system's actuation during force testing. The force sensor is attached to the top plate and the force detected by the sensor is sent directly to the laptop.

Data may be taken from the universal joint attached to the robotic system. The data recorded was applied to three different rotational movements in a 3D space. The universal joint accomplished movements in 3D to present increased flexibility in all directions. The rotational movements recorded by the universal joint include roll, pitch and yaw. The experiment was established to ensure stability, maneuverability and efficiency. Position data was recorded and determined in MATLAB. For all movements, there is an experimental movement of the universal joint on the ultrasound robot and a desired path of the universal joint. Beside the position data, the roll, pitch and yaw data are also included as well as the error between the measured and the modeled results.

To test the prototype, the movable platform 802 was made to move along several different trajectories. The hybrid, cable-driven passive soft link ultrasound robot can perform complex movements, which provides increased functionality and improved accuracy. The experimental trajectories recorded in this disclosure included circle, square and helical trajectories, although any trajectories can be used, limited only by the constraints of the system. For each of these demonstration trajectories, the experimental data is projected along with the planned trajectory. Alongside the trajectories is the error along the X, and Y axes and also for the helical trajectory, the Z axis. Position data analysis and graphing was performed in MATLAB.

A basic force profile that may be collected from the soft robotic system. In one example profile was created using one of the experimental setups detailed elsewhere in this disclosure. The force profile was taken for two different versions of the cable-driven robotic system: one with three passive arms and one with six passive arms. Examples of such a robot type are displayed schematically in FIG. 12 (three link design) and FIG. 13 (six link design), with the cables 904, the passive soft links 902, the movable platform 802, and the base 808 as labelled.

The data was taken using various circular trajectories with radii of 5.0 cm, 2.5 cm, and 1.0 cm. The data was also taken at the normal operating height at both systems. The data was taken by actuating the cables to move the top plate in said circles stopping ten times in every circle. After completing one circuit of the motion, a bit of tension from the cables was released which caused the upper platform of the system to drift up slightly. The force sensor is placed on the top as it drifts upward and the force at that point is then recorded digitally using MeasureLite software. The trajectory stopping points are shown diagrammatically in FIG. 17.

Figure 17:
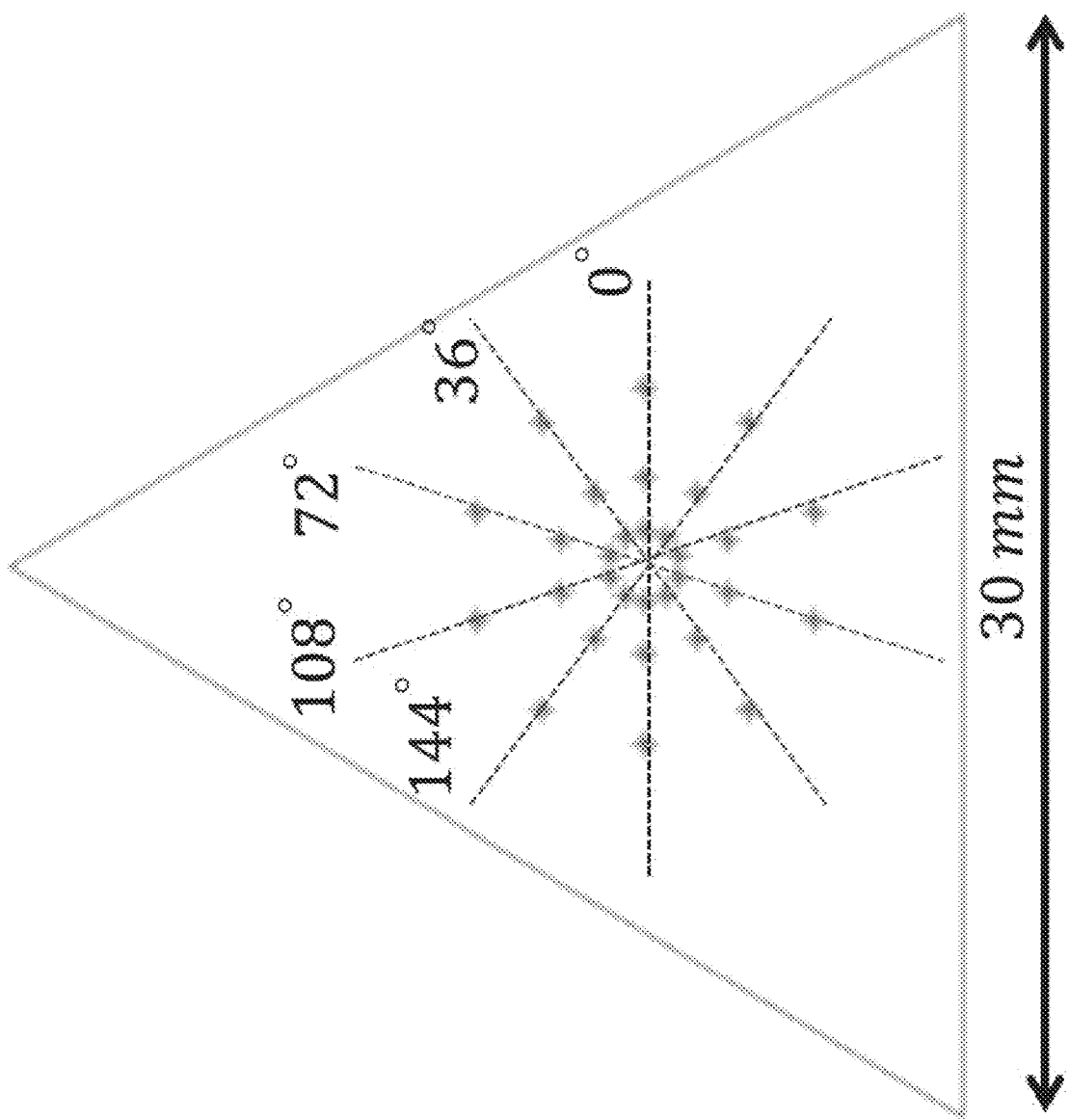
FIG. 17 illustrates the range of motion experiment for the soft robots.

The three circles of plus signs in FIG. 17 at different radii represent the stopping points where the force data were recorded. The points of the triangle represent the placement of each of the servos in the baseplate of the hybrid soft cable driven robot. The data were recorded starting at the rightmost point of the largest circle, clockwise around the largest circle, then inward to the smaller circle. The data from the testing is displayed in Tables 1 and 2.

TABLE 1

Test data from Six Support Structure. Max = 6.69N, Min = 6.25N

| | Radius(mm) | | | | | |
|---|---|---|---|---|---|---|
| Angle (deg) | 5 | 2.5 | 1 | 1 | 2.5 | 5 |
| 0 | 6.66N | 6.47N | 6.25N | 6.36N | 6.47N | 6.61N |
| 36 | 6.50N | 6.55N | 6.74N | 6.58N | 6.57N | 6.49N |
| 72 | 6.45N | 6.51N | 6.50N | 6.50N | 6.57N | 6.51N |
| 108 | 6.64N | 6.62N | 6.54N | 6.45N | 6.69N | 6.57N |
| 144 | 6.61N | 6.52N | 6.61N | 6.48N | 6.61N | 6.57N |

TABLE 2

Test data from Three Support Structure. Max = 2.92N, Min = 2.64N

| | Radius (mm) | | | | | |
|---|---|---|---|---|---|---|
| Angle (deg) | 5 | 2.5 | 1 | 1 | 2.5 | 5 |
| 0 | 2.73N | 2.76N | 2.74N | 2.74N | 2.91N | 2.79N |
| 36 | 2.82N | 2.78N | 2.76N | 2.81N | 2.75N | 2.81N |
| 72 | 2.75N | 2.81N | 2.82N | 2.76N | 2.73N | 2.72N |
| 108 | 2.85N | 2.92N | 2.69N | 2.77N | 2.89N | 2.81N |
| 144 | 2.85N | 2.84N | 2.86N | 2.84N | 2.64N | 2.64N |

Table 1 covers force data from the six-support setup and Table 2 covers force data from the three-support setup. The data across all three circles for both the six-support and the three-support setup are quite consistent. Each column represents the force measured when the platform was moved along a circle of the stated radius (1 mm, 2.5 mm, or 5 mm). The six-support setup produces a constant force of approximately 6.6 N at all data points tested. The three-support setup produces a constant force of approximately 2.7 N at all data points tested. There were no large spikes of force in the data at any tested point, showing that the system's supportive force output is constant across the central workspace. The force could be alerted by doing this trajectory at a different Z point making it closer or farther from the baseplate. The number of soft supports could also be changed until the desired static supporting force is reached.

This disclosure reports on the design, modeling, and manufacturing of several different novel 3D soft robots that are analogous to a rigid Delta robot. All these soft robots place an end-effector on a platform, and move the platform, or use the platform as an end-effector. A first soft robot was designed using three arms with tendon-driven actuators to flex inwards or outwards and thereby control the X, Y, and Z locations of a mobile platform. A second soft robot was designed using six arms, paired. The bottom portion of these six arms had similar tendon-drive actuators and the upper portions of these six arms each had a passive rigid or semi-rigid link to a mobile platform. By actuating these flexible links of the six arms, the upper platform could be translated or rotated with six degrees of freedom. A third exemplary soft robot was designed and fabricated using a passive soft link 902 and cables 904. The mobile platform 802 was connected by three pairs of compressed passive soft links 902 to a base 808. Cables 904 driven by servo-motors 812, 814, 816 provide tension to counter-act the compression of the passive soft links 902. By changing the tension of the cables 904 the movable platform can be translated in three dimensions. With additional cables and servo-motors, it is, in principle, possible to provide rotation about three axes (three additional degrees of freedom), as was demonstrated by the second soft robot. Rotation of the mobile platform (or just the end-effector) about three axes may also be provided by a universal joint controlled by additional motors thus providing six degrees of freedom.

Figure 18:
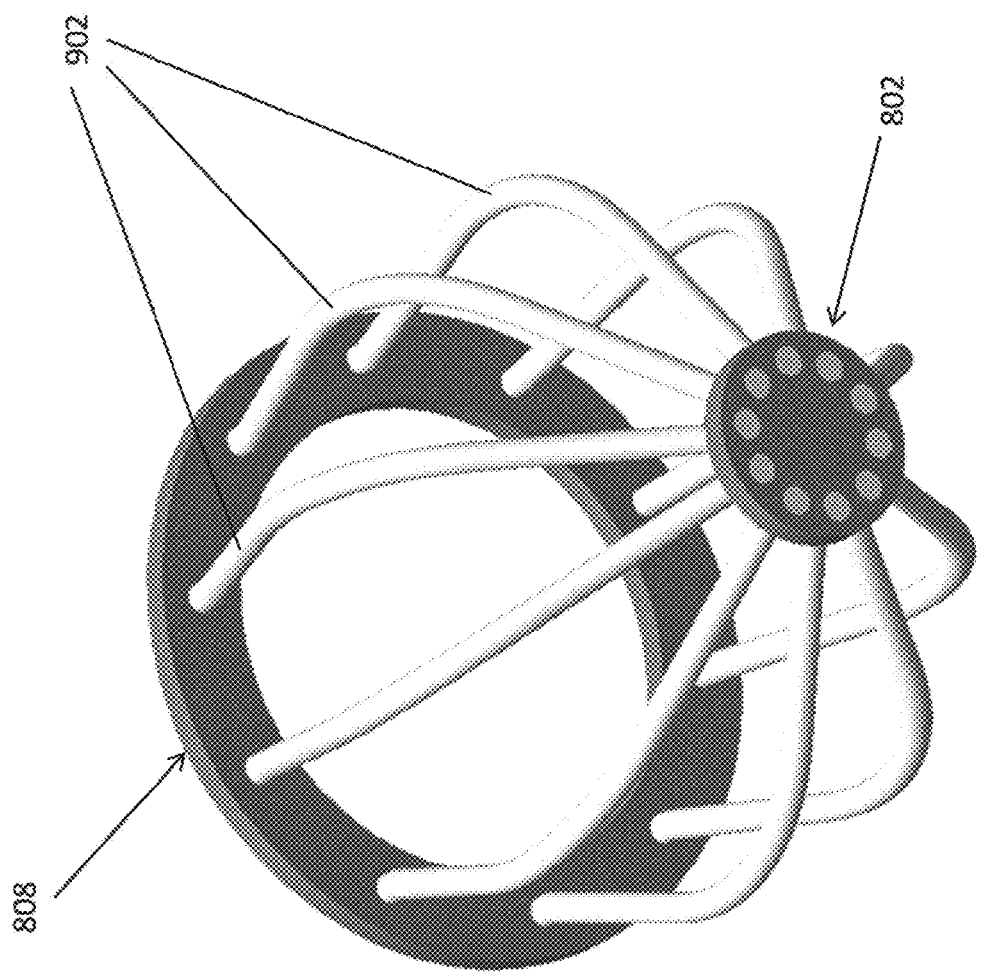
FIG. 18 illustrates an exemplary soft robot with 10 legs for additional stability.

FIG. 18 illustrates an exemplary soft passive link type robot with more than three passive limbs. As illustrated, the larger, fixed base 808 is on top and the movable platform 802 is on the bottom, so that the passive links 902 might be considered "legs" (pointing downwards) rather than "arms" (pointing upwards). In general, such passive soft links 902 may also be called "limbs." The cables 904 which provide motion are not illustrated in FIG. 18 to emphasize the additional limbs. Additional limbs may provide motion for additional degrees of freedom, when coupled with independent drive cables, or may provide improved stability or enhance the uniformity of the force applied from the robot to a patient.

Figure 19:
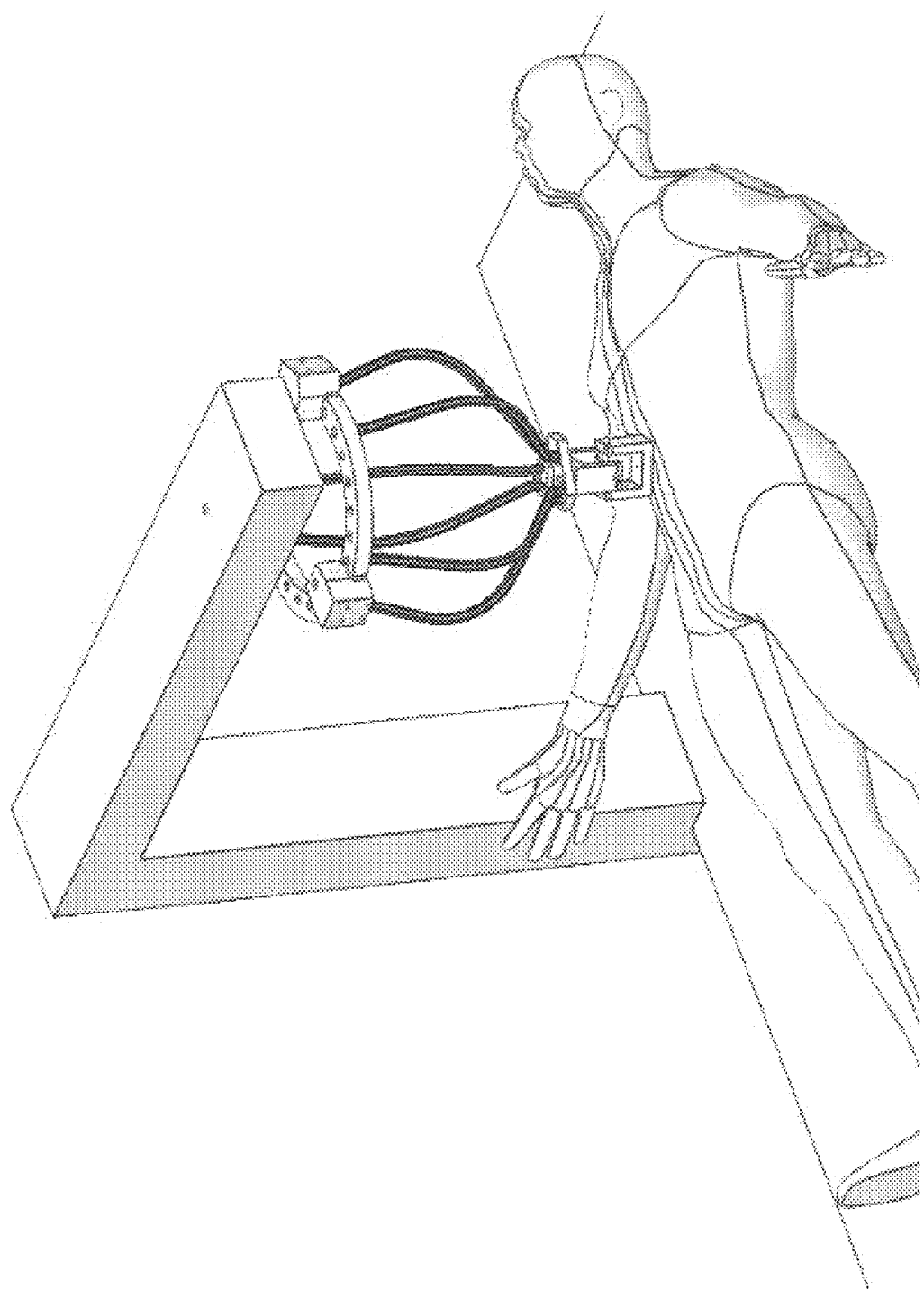
FIG. 19 illustrates an exemplary soft robot being used for ultrasound on a patient's abdomen.

FIG. 19 illustrates an exemplary 6-arm robot mounted on a frame with a patient on an examination table. In the illustration, the movable platform 802 has a universal joint with two angular degrees of freedom while the 3 translation degrees of freedom are provided by the six passive soft links and the cables driven by servo-motors. (The cables and the motors are not shown in the figure.) An ultrasound unit may be mounted as an end effector onto the universal joint or onto the mobile platform. A person could control the robot ultrasound system remotely and the human patient would not be subjected to a large enough force to be damaged, while still providing enough force for the ultrasound measurement to be accurate and useful. In the illustration, the ultrasound is taking an image of the patient's abdomen.

The exemplary soft robots described in this disclosure consist of at least three closed kinematic chains that connect the upper platform to the bottom platform through various links and joints. The three exemplary soft robots were fabricated by 3D printed using TPU and other materials. The upper platform was controlled through the actuation of the tendon driven soft links (for the first two robots) or by means of cables attached to the upper platform in conjunction with a set of passive soft links. The kinematics models of these robots were derived based on the constant curvature assumption and the simulation results showed that these robots can move in 3D trajectories and with the six-armed version can also provide rotations about three axes. The dynamics of the soft robots were simulated using Simscape. A comparison of the experimental data and simulation results indicates the effectiveness of the Simscape model.

The Present Disclosure Comprises at Least the Following Aspects:

Aspect 1: A device comprising: a controllable platform; one or more arms coupled to the platform and configured to facilitate controlled movement of the platform in multiple degrees of freedom, wherein the one or more arms comprise at least one flexible link; a base spaced from the platform and coupled to the one or more arms; and a controller operationally coupled to the at least one flexible link and configured to cause movement of the at least one flexible link to control one or more of an orientation or a position of the platform.

Aspect 2: The device of aspect 1, wherein the flexible links are made from materials comprising thermoplastic polyurethane, or the like.

Aspect 3: The device of any one of aspects 1-2, wherein the flexible links are soft tendon driven actuators.

Aspect 4: The device of any one of aspects 1-2, wherein the flexible links are soft pneumatic actuators.

Aspect 5: The device of any one of aspects 1-4, further comprising a joystick controller for controlling the motion in 6 DOF.

Aspect 6: The device of aspect 5, wherein the joystick controller uses quantitative feedback theory.

Aspect 7: The device of any one of aspects 5-6, wherein the joystick controller is a Stewart mechanism.

Aspect 8: The device of aspect 7, further comprising one or more linear potentiometers mounted onto one or more onto the legs of the Stewart mechanism.

Aspect 9: The device of any one of aspects 1-8, wherein the device is configured to cover an area above an abdomen of a patient.

Aspect 10: device of any one of aspects 1-9, further comprising an ultrasound imaging apparatus.

Aspect 11: A method of making the device of any one of aspects 1-10.

Aspect 12: An apparatus comprising a base; a platform comprising an end-effector; one or more arms connecting the platform to the base, wherein the one or more arms comprise a flexible link and a passive link; one or more motors adjacent to the base; one or more cables connecting the one or more flexible links to the one or more motors; and a controller for actuating the one or more motors, wherein the controller actuates the one or more motors to controllably decrease or controllably increase the tension in the one or more cables and thereby flex each flexible link as needed to move the end-effector to a selected location and to rotate the end-effector to a selected orientation.

Aspect 13: The apparatus of aspect 12, wherein the one or more arms are arranged in a threefold symmetric pattern around the base.

Aspect 14: The apparatus of any one of aspects 12-13, wherein the arms are fabricated using a 3D printed thermoplastic.

Aspect 15: The apparatus of any one of aspects 12-14, wherein the end-effector comprises an ultrasound imaging apparatus.

Aspect 16: The apparatus of any one of aspects 12-15, wherein a tension for a selected one or more cables is controlled by a selected one or more motors.

Aspect 17: The apparatus of any one of aspects 12-16, further comprising a feedback means for controlling the location and the orientation of the end-effector.

Aspect 18: The apparatus of any one of aspects 12-17, wherein the feedback means comprises an electromagnetic tracker.

Aspect 19: A method of making the apparatus of any one of aspects 12-18.

Aspect 20: A soft cable-driven parallel robot apparatus comprising: a base; a movable platform comprising an end-effector; one or more passive soft links connecting the platform to the base, wherein the one or more passive soft links are in compression to push the platform away from the base; one or more motors adjacent to the base; one or more cables connected to the platform and to the one or more motors; and a controller for actuating each the one or more motors, wherein the controller actuates the one or more motors to controllably decrease or controllably increase a tension in the one or more cables, whereby the one or more passive soft links move the end-effector to a selected location.

Aspect 21: The apparatus of aspect 20, wherein the one or more passive links are arranged in a threefold symmetric pattern around the base.

Aspect 22: The apparatus of any one of aspects 20-21, further comprising one or more motor-controlled universal joints for orienting the end-effector.

Aspect 23: The apparatus of any one of aspects 20-22, wherein the end-effector comprises an ultrasound imaging apparatus.

Aspect 24: The apparatus of any one of aspects 20-23, wherein the controller actuates the one or more motors to provide tension for the one or more cables to place the end-effector in a selected location.

Aspect 25: The apparatus of aspect 24, wherein controller further actuates the one or more motors to provide tension for the one or more cables to place the end-effector in a selected orientation.

Aspect 26: The apparatus of any one of aspects 20-25, further comprising a feedback means for controlling the selected location and the selected orientation of the end-effector.

Aspect 27: The apparatus of aspect 26, wherein the feedback means comprises an electromagnetic tracker.

Aspect 28: A method of making the apparatus of any one of aspects 20-27.

What is claimed is:

1. A soft cable-driven parallel robot apparatus comprising:
   a base;
   a movable platform comprising an end-effector;
   a plurality of passive soft links connecting the platform to the base, wherein the plurality of passive soft links are in compression to push the platform away from the base;
   one or more motors adjacent to the base;
   one or more cables connected to the movable platform and to the one or more motors; and
   a controller for actuating the one or more motors, wherein the controller actuates the one or more motors to controllably decrease or controllably increase tension in the one or more cables, whereby the cables and the plurality of passive soft links control the position and orientation of the moveable platform, and are further configured to move the end-effector to a selected location.

2. The apparatus of claim 1, wherein the plurality of passive soft links is arranged in a threefold symmetric pattern around the base.

3. The apparatus of claim 1, further comprising one or more motor-controlled universal joints for orienting the end-effector.

4. The apparatus of claim 1, wherein the end-effector comprises an ultrasound imaging apparatus.

5. The apparatus of claim 1, further comprising a feedback means for controlling the selected location and the selected orientation of the end-effector.

6. The apparatus of claim 5, wherein the feedback means comprises an electromagnetic tracker.

* * * * *